United States Patent
Barnett et al.

[11] Patent Number: 5,824,532
[45] Date of Patent: Oct. 20, 1998

[54] OXIDATIVLEY STABLE ALPHA-AMYLASE

[75] Inventors: Christopher C. Barnett, South San Francisco; Colin Mitchinson, Half Moon Bay; Scott D. Power, San Bruno; Carol A. Requadt, Tiburon, all of Calif.

[73] Assignee: Genencor International, Inc., Rochester, N.Y.

[21] Appl. No.: 468,220

[22] Filed: Jun. 6, 1995

Related U.S. Application Data

[60] Division of Ser. No. 194,664, Feb. 10, 1994, which is a continuation-in-part of Ser. No. 16,395, Feb. 11, 1993, abandoned.

[51] Int. Cl.⁶ .............................. C12N 15/56; C12N 9/28; C12N 1/21; C12N 15/63
[52] U.S. Cl. ..................... 435/202; 435/201; 435/203; 435/204; 435/172.3; 435/71.2; 435/252.3; 435/252.31; 435/320.1; 536/23.2; 536/23.7
[58] Field of Search ...................... 435/201, 202, 435/203, 204, 172.3, 71.2, 252.3, 252.31, 320.1; 536/23.2, 23.7

[56] References Cited

U.S. PATENT DOCUMENTS

| | | | |
|---|---|---|---|
| 4,261,868 | 4/1981 | Hora et al. | 252/529 |
| 4,284,722 | 8/1981 | Tamuri et al. | 435/94 |
| 4,493,893 | 1/1985 | Mielenz et al. | 435/172.3 |
| 4,620,936 | 11/1986 | Kielman et al. | 252/99 |
| 4,634,551 | 1/1987 | Burns et al. | 252/102 |
| 4,732,973 | 3/1988 | Barr et al. | 530/350 |
| 4,752,585 | 6/1988 | Koths et al. | 435/256 |
| 4,760,025 | 7/1988 | Estell et al. | 435/256 |
| 4,863,626 | 9/1989 | Coyne et al. | 252/91 |
| 5,118,623 | 6/1992 | Boguslawski et al. | 435/222 |
| 5,346,823 | 9/1994 | Estell et al. | 435/222 |

FOREIGN PATENT DOCUMENTS

| | | |
|---|---|---|
| 0946/92 | 7/1992 | Denmark. |
| 1503/92 | 12/1992 | Denmark. |
| 0 130 756 | 1/1985 | European Pat. Off.. |
| 0 285 123 | 5/1988 | European Pat. Off.. |
| 0 409 299 | 1/1991 | European Pat. Off.. |
| 0 410 498 | 1/1991 | European Pat. Off.. |
| 0 676 456 | 11/1992 | France. |
| 91/00353 | 1/1991 | WIPO. |
| 91/16423 | 10/1991 | WIPO. |
| 92/08778 | 5/1992 | WIPO. |
| 92/11286 | 7/1992 | WIPO. |
| 94/02597 | 2/1994 | WIPO. |

OTHER PUBLICATIONS

Y. Matsuura et al., "Structure and Possible Catalytic Residues of Taka–Amylase A", J. Biochemistry 95: 697–702, (1984).

G. Gray et al., "Structural Gene Encoding the Thermophillic α–Amylases of *Bacillus stearothermophilus* and *Bacillus licheniformis*", J. Bact. 166(2) 635–643, (May 1986).

L. Holn et al., "Random Mutagenesis used to Probe the Structure and Function of *Bacillus stearothermophilus* Alpha Amylase", Prot. Engineering 3(3) 181–191 (1990).

(List continued on next page.)

*Primary Examiner*—Rebecca E. Prouty
*Attorney, Agent, or Firm*—Christopher L. Stone

[57] ABSTRACT

Novel alpha-amylase mutants derived from the DNA sequences of naturally occurring or recombinant alpha-amylases are disclosed. The mutant alpha-amylases, in general, are obtained by in vitro modifications of a precursor DNA sequence encoding the naturally occurring or recombinant alpha-amylase to generate the substitution (replacement) or deletion of one or more oxidizable amino acid residues in the amino acid sequence of a precursor alpha-amylase. Such mutant alpha-amylases have altered oxidative stability and/or altered pH performance profiles and/or altered thermal stability as compared to the precursor. Also disclosed are detergent and starch liquefaction compositions comprising the mutant amylases, as well as methods of using the mutant amylases.

11 Claims, 22 Drawing Sheets

OTHER PUBLICATIONS

A. Rudolphus et al., "Oxidation–Resistant Variants of Recombinant Antileucoprotease Are Better Inhibitors of Human Neutrophil Elastase Induced Emphysema in Hamsters Than Natural Recombinant Antileucoprotease", Clinical Science 81(6): 777–784, Dec. 1991.

Bealinkelly et al, "Studies on the thermostability of the alpha–amylase of bacillus–caldovelox" Appl. Microbiol. and Biotech 36(3):332–336 (Dec. 1991).

Brosnan, et al., "Investigation of the mechanism of irreversible thermoinactivation of bacillus–stearothermophilus alpha–amylase" Eur. J. of Biochem. 203(1–2)225–231 (Jan. 1992).

Declerck, et al., "Use of Amber Suppressors to Investigate the Thermostability of *Bacillus licheniformis* α–Amylase" J. Biol. Chem. 265(26):15481–15488 (1990).

Estell, et al., "Engineering an enzyme by Site–directed Mutagenesis to Be Resistant to Chemical Oxidatin" J. of Biol. Chem. 260(11)6518–6521 (Jun. 1985).

Janecek, et al., "α–Amylases and approaches leading to their enhanced stability" FEBS 11085 304(1,1–3):1–3 (Jun. 1992).

Jorgenesen, "Cloning of a chromosomal α–amylase gene from *Bacillus stearothermophilus*" FEMS Microbiology Letters 77:271–276 (1991).

Joyet, et al., "Hyperthermostable variants of a highly thermostable alpha–amylase" Biotechnology 10:1579–1583 (Dec. 1992).

Manning, et al., "Thermostable α–Amyulase of *Bacillus stearothermophilus*" J. of Biol. Chem. 236(11):2952–2965 (Nov. 1961).

Matsui et al., "A mutant α–amylase with enhanced activity specific for short substrates" FEBS 11596 310(3):216–218 (Oct. 1992).

Matsui et al., "An increase in the transglycosylation activity of *Saccharomycopsis* α–amylase altered by site–directed mutagenesis" Biochemica et Biophysica Acta 1077:416–419 (1991).

Nakajima, et al., "Nucleotide Sequence of the *Bacillus stearothermophilus* α–Amylase Gene" J. Bacteriology 163(1):401–406 (Jul. 1985).

Ogasahara, et al., "Studies on Thermophilic α–Amylase from *Bacillus stearothermophilus*" J. Biochem. 67(1):65–89 (1970).

Ottesen et al., "The Subtilisins" Methods in Enzymology 19:199–215.

Sogaard et al., "Site–directed Mutagenesis of Histidine 93, Aspartic Acid 180, Glutamic Acid 205, Histidine 290, and Aspartic Acid 291 at the Active Site and Tryphtophan 279 at the Raw Starch Binding site in Barley α–Amylase 1" J. Biol. chem. 268(32) 22480–22484 (Oct. 1993).

Suzuki, et al., "Amino Acid Residues Stabilizing a *Bacillus* α–Amylase agaimst Irreversible Thermoinactivation" J. Biol. Chem. 264(32):18933–18938 (Nov. 1989).

Svensson, et al., "Mutational analysis of glucosylase function" J. Biotech. 29:1–37 (1993).

Takase et al., "Site–directed mutagensis of active site residues in *Bacillus subtilis a–amylase*" Biochimica et Biophysica Acta 1120–281–288 (1992).

Tomazic et al., "Mechansims of Irreversible thermal Inactivation of *Bacillus* α–Amylases" J. of Biol. Chem. 262(7):3086–3091 (Mar. 1988).

Vihinen et al. "Site–Directed Mutagenesis of a Thermostable α–Amylases from *Bacillus stearothermophilus*: Punitive Role of Three Conserved Residues" J. Biochem 107:267–272 (1990).

```
                10                        30                          50
AGCTTGAAGAAGTGAAGAAGCAGAGAGGCTATTGAATAAATGAGTAGAAAGCGCCATATC 70                        90                         110
GGCGCTTTTCTTTTGGAAGAAAATATAGGGAAAATGGTACTTGTTAAAAATTCGGAATAT 130                       150                         170
TTATACAACATCATATGTTTCACATTGAAAGGGGAGGAGAATCATGAAACAACAAAAACG
                                                 M   K   Q   Q   K   R
               190                       210                         230
GCTTTACGCCCGATTGCTGACGCTGTTATTTGCGCTCATCTTCTTGCTGCCTCATTCTGC
 L   Y   A   R   L   L   T   L   L   F   A   L   I   F   L   L   P   H   S   A
               250                       270                         290
AGCAGCGGCGGCAAATCTTAATGGGACGCTGATGCAGTATTTTGAATGGTACATGCCCAA
 A   A   A   N   L   N   G   T   L   M   Q   Y   F   E   W   Y   M   P   N
               310                       330                         350
TGACGGCCAACATTGGAAGCGTTTGCAAAACGACTCGGCATATTTGGCTGAACACGGTAT
 D   G   Q   H   W   K   R   L   Q   N   D   S   A   Y   L   A   E   H   G   I
               370                       390                         410
TACTGCCGTCTGGATTCCCCCGGCATATAAGGGAACGAGCCAAGCGGATGTGGGCTACGG
 T   A   V   W   I   P   P   A   Y   K   G   T   S   Q   A   D   V   G   Y   G
               430                       450                         470
TGCTTACGACCTTTATGATTTAGGGGAGTTTCATCAAAAAGGGACGGTTCGGACAAAGTA
 A   Y   D   L   Y   D   L   G   E   F   H   Q   K   G   T   V   R   T   K   Y
               490                       510                         530
CGGCACAAAAGGAGAGCTGCAATCTGCGATCAAAAGTCTTCATTCCCGCGACATTAACGT
 G   T   K   G   E   L   Q   S   A   I   K   S   L   H   S   R   D   I   N   V
               550                       570                         590
TTACGGGGATGTGGTCATCAACCACAAAGGCGGCGCTGATGCGACCGAAGATGTAACCGC
 Y   G   D   V   V   I   N   H   K   G   G   A   D   A   T   E   D   V   T   A
               610                       630                         650
GGTTGAAGTCGATCCCGCTGACCGCAACCGCGTAATTTCAGGAGAACACCTAATTAAAGC
 V   E   V   D   P   A   D   R   N   R   V   I   S   G   E   H   L   I   K   A
               670                       690                         710
CTGGACACATTTTCATTTTCCGGGGCGCGGCAGCACATACAGCGATTTTAAATGGCATTG
 W   T   H   F   H   F   P   G   R   G   S   T   Y   S   D   F   K   W   H   W
               730                       750                         770
GTACCATTTTGACGGAACCGATTGGGACGAGTCCCGAAAGCTGAACCGCATCTATAAGTT
 Y   H   F   D   G   T   D   W   D   E   S   R   K   L   N   R   I   Y   K   F
               790                       810                         830
TCAAGGAAAGGCTTGGGATTGGGAAGTTTCCAATGAAAACGGCAACTATGATTATTTGAT
 Q   G   K   A   W   D   W   E   V   S   N   E   N   G   N   Y   D   Y   L   M
```

FIG._1A

```
                850                  870                   890
GTATGCCGACATCGATTATGACCATCCTGATGTCGCAGCAGAAATTAAGAGATGGGGCAC
 Y   A   D   I   D   Y   D   H   P   D   V   A   A   E   I   K   R   W   G   T
                910                  930                   950
TTGGTATGCCAATGAACTGCAATTGGACGGTTTCCGTCTTGATGCTGTCAAACACATTAA
 W   Y   A   N   E   L   Q   L   D   G   F   R   L   D   A   V   K   H   I   K
                970                  990                   1010
ATTTTCTTTTTTGCGGGATTGGGTTAATCATGTCAGGGAAAAAACGGGGAAGGAAATGTT
 F   S   F   L   R   D   W   V   N   H   V   R   E   K   T   G   K   E   M   F
                1030                 1050                  1070
TACGGTAGCTGAATATTGGCAGAATGACTTGGGCGCGCTGGAAAACTATTTGAACAAAAC
 T   V   A   E   Y   W   Q   N   D   L   G   A   L   E   N   Y   L   N   K   T
                1090                 1110                  1130
AAATTTTAATCATTCAGTGTTTGACGTGCCGCTTCATTATCAGTTCCATGCTGCATCGAC
 N   F   N   H   S   V   F   D   V   P   L   H   Y   Q   F   H   A   A   S   T
                1150                 1170                  1190
ACAGGGAGGCGGCTATGATATGAGGAAATTGCTGAACGGTACGGTCGTTTCCAAGCATCC
 Q   G   G   G   Y   D   M   R   K   L   L   N   G   T   V   V   S   K   H   P
                1210                 1230                  1250
GTTGAAATCGGTTACATTTGTCGATAACCATGATACACAGCCGGGGCAATCGCTTGAGTC
 L   K   S   V   T   F   V   D   N   H   D   T   Q   P   G   Q   S   L   E   S
                1270                 1290                  1310
GACTGTCCAAACATGGTTTAAGCCGCTTGCTTACGCTTTTATTCTCACAAGGGAATCTGG
 T   V   Q   T   W   F   K   P   L   A   Y   A   F   I   L   T   R   E   S   G
                1330                 1350                  1370
ATACCCTCAGGTTTTCTACGGGGATATGTACGGGACGAAAGGAGACTCCCAGCGCGAAAT
 Y   P   Q   V   F   Y   G   D   M   Y   G   T   K   G   D   S   Q   R   E   I
                1390                 1410                  1430
TCCTGCCTTGAAAACACAAAATTGAACCGATCTTAAAAGCGAGAAAACAGTATGCGTACGG
 P   A   L   K   H   K   I   E   P   I   L   K   A   R   K   Q   Y   A   Y   G
                1450                 1470                  1490
AGCACAGCATGATTATTTCGACCACCATGACATTGTCGGCTGGACAAGGGAAGGCGACAG
 A   Q   H   D   Y   F   D   H   H   D   I   V   G   W   T   R   E   G   D   S
                1510                 1530                  1550
CTCGGTTGCAAATTCAGGTTTGGCGGCATTAATAACAGACGGACCCGGTGGGGCAAAGCG
 S   V   A   N   S   G   L   A   A   L   I   T   D   G   P   G   G   A   K   R
                1570                 1590                  1610
AATGTATGTCGGCCGGCAAAACGCCGGTGAGACATGGCATGACATTACCGGAAACCGTTC
 M   Y   V   G   R   Q   N   A   G   E   T   W   H   D   I   T   G   N   R   S
                1630                 1650                  1670
GGAGCCGGTTGTCATCAATTCGGAAGGCTGGGGAGAGTTTCACGTAAACGGCGGGTCGGT
 E   P   V   V   I   N   S   E   G   W   G   E   F   H   V   N   G   G   S   V
```

FIG._1B

```
            1690                  1710                   1730
TTCAATTTATGTTCAAAGATAGAAGAGCAGAGAGGACGGATTTCCTGAAGGAAATCCGTT
 S   I   Y   V   Q   R   *
            1750                  1770                   1790
TTTTTATTTTGCCCGTCTTATAAATTTCTTTGATTACATTTTATAATTAATTTTAACAAA 1810                  1830                   1850
GTGTCATCAGCCCTCAGGAAGGACTTGCTGACAGTTTGAATCGCATAGGTAAGGCGGGGA 1870                  1890                   1910
TGAAATGGCAACGTTATCTGATGTAGCAAAGAAAGCAAATGTGTCGAAAATGACGGTATC 1930                  1950
GCGGGTGATCAATCATCCTGAGACTGTGACGGATGAATTGAAAAAGCT
```

FIG._1C

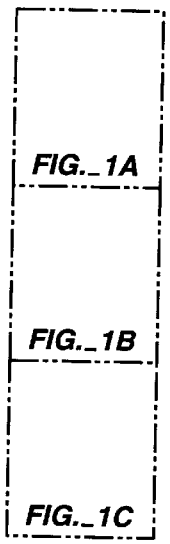

FIG._1

```
           10                    30                    50
ANLNGTLMQYFEWYMPNDGQHWKRLQNDSAYLAEHGITAVWIPPAYKGTSQADVGYGAYD 70                    90                   110
LYDLGEFHQKGTVRTKYGTKGELQSAIKSLHSRDINVYGDVVINHKGGADATEDVTAVEV 130                   150                   170
DPADRNRVISGEHLIKAWTHFHFPGRGSTYSDFKWHWYHFDGTDWDESRKLNRIYKFQGK 190                   210                   230
AWDWEVSNENGNYDYLMYADIDYDHPDVAAEIKRWGTWYANELQLDGFRLDAVKHIKFSF 250                   270                   290
LRDWVNHVREKTGKEMFTVAEYWQNDLGALENYLNKTNFNHSVFDVPLHYQFHAASTQGG 310                   330                   350
GYDMRKLLNGTVVSKHPLKSVTFVDNHDTQPGQSLESTVQTWFKPLAYAFILTRESGYPQ 370                   390                   410
VFYGDMYGTKGDSQREIPALKHKIEPILKARKQYAYGAQHDYFDHHDIVGWTREGDSSVA 430                   450                   470
NSGLAALITDGPGGAKRMYVGRQNAGETWHDITGNRSEPVVINSEGWGEFHVNGGSVSIY

VQR
```

FIG._2

Am-Lich = B.Licheniformis    Am-Amylo = B.amyloliquefaciens    Am-Stearo = B.stearothermophilus

```
                                                                                    19
                                                                                     1
Am-Lich     ........MKQQ  KRLYARLLTL  LFALIFLLPH  ..........  .......SAAA  AANLNGTLMQ  YFEWYMPNDG
Am-Amylo    MRGRGNMIQK    RKRTVSFRLV  LMCTLLFVSL  ..........  .......PITK  TSAVNGTLMQ  YFEWYTPNDG
Am-Stearo   .......VLTF   HRIIRKGWMF  LLAFLLTASL  FCPTGRHAKA  AAPFNGTMMQ   YFEWYLPDDG
                                                                                    60
                                                                                    79
                                                                                   120
Am-Lich      61
            QHWKRLQNDS    AYLAEHGITA  VWIPPAYKGT  SQADVGYGAY  DLYDLGEFHQ   KGTVRTKYGT
Am-Amylo    QHWKRLQNDA    EHLSDIGITA  VWIPPAYKGL  SQSDNGYGPY  DLYDLGEFQQ   KGTVRTKYGT
Am-Stearo   TLWTKVANEA    NNLSSLGITA  LSLPPAYKGT  SRSDVGYGVY  DLYDLGEFNQ   KGTVRTKYGT
                                                                                   139
                                                                                   180
Am-Lich      121
            KGELQSAIKS    LHSRDINVYG  DVVINHKGGA  DATEDVTAVE  VDPADRNRVI   SGEHLIKAWT
Am-Amylo    KSELQDAIGS    LHSRNVQVYG  DVVLNHKAGA  DATEDVTAVE  VNPANRNQET   SEEYQIKAWT
Am-Stearo   KAQYLQAIQA    AHAAGMQVYA  DVVFDHKGGA  DGTEWVDAVE  VNPSDRNQEI   SGTYQIQAWT
                                                                                   197
                                                                                   240
Am-Lich      181
            HFHFPGRGST    YSDFKWHWYH  FDGTDWDESR  KLNRIYKF... QGKAWDWEVS   NENGNYDYLM
Am-Amylo    DFRFPGRGNT    YSDFKWHWYH  FDGADWDESR  KISRIFKFRG  EGKAWDWEVS   SENGNYDYLM
Am-Stearo   KFDFPGRGNT    YSSFKWRWYH  FDGVDWDESR  KLSRIYKFRG  IGKAWDWEVD   TENGNYDYLM
                                                                                   257
                                                                                   300
Am-Lich      241
            YADIDYDHPD    VAAEIKRWGT  WYANELQLDG  FRLDAVKHIK  FSFLRDWVNH   VREKTGKEMF
Am-Amylo    YADVDYDHPD    VVAETKKWGI  WYANELSLDG  FRIDAAKHIK  FSFLRDWVQA   VRQATGKEMF
Am-Stearo   YADLDMDHPE    VVTELKNWGK  WYVNTTNIDG  FRLDGLKHIK  FSFFPDWLSY   VRSQTGKPLF
                                                                                   317
                                                                                   360
Am-Lich      301
            TVAEYWQNDL    GALENYLNKT  NFNHSVFDVP  LHYQFHAAST  QGGGYDMRKL   LNGTVVSKHP
Am-Amylo    TVAEYWQNNA    GKLENYLNKT  SFNQSVFDVP  LHFNLQAASS  QGGGYDMRRL   LDGTVVSRHP
Am-Stearo   TVGEYWSYDI    NKLHNYITKT  NGTMSLFDAP  LHNKFYTASK  SGGAFDMRTL   MTNTLMKDQP
```

FIG. _3A

```
              361
Am-Lich       LKSVTFVDNH DTQPGQSLES TVQTWFKPLA YAFILTRESG YPQVFYGDMY GTKGDSQREI    377
Am-Amylo      EKAVTFVENH DTQPGQSLES TVQTWFKPLA YAFILTRESG YPQVFYGDMY GTKGTSPKEI    420
Am-Stearo     TLAVTFVDNH DTNPAKR..CS HGRPWFKPLA YAFILTRQEG YPCVFYGDYY GI.......PQYNI 421                                                                  437
Am-Lich       PALKHKIEPI LKARKQYAYG AQHDYFDHHD IVGWTREGDS SVANSGLAAL ITDGPGGAKR    480
Am-Amylo      PSLKDNIEPI LKARKEYAYG PQHDYIDHPD VIGWTREGDS SAAKSGLAAL ITDGPGGSKR
Am-Stearo     PSLKSKIDPL LIARRDYAYG TQHDYLDHSD IIGWTREGVT EKPGSGLAAL ITDGAGRSKW 481                                                                  540
Am-Lich       MYVGRQNAGE TWHDITGNRS EPVVINSEGW GEFHVNGGSV SIYVQR.....               483
Am-Amylo      MYAGLKNAGE TWYDITGNRS DTVKIGSDGW GEFHVNDGSV SIYVQK.....
Am-Stearo     MYVGKQHAGK VFYDLTGNRS DTVTINSDGW GEFKVNGGSV SVWVPRKTTV STIARPITTR 541         559
Am-Lich       .......... .........
Am-Amylo      .......... .........
Am-Stearo     PWTGEFVRWH EPRLVAWP*
```

*FIG._3B*

| FIG._3A |
|---------|
| FIG._3B |

*FIG._3*

```
           10                    30                    50
ANLNGTLMQYFEWYMPNDGQHWKRLQNDSAYLAEHGITAVWIPPAYKGTSQADVGYGAYD 70                    90                   110
LYDLGEFHQKGTVRTKYGTKGELQSAIKSLHSRDINVYGDVVINHKGGADATEDVTAVEV 130                   150                   170
DPADRNRVISGEHLIKAWTHFHFPGRGSTYSDFKWHWYHFDGTDWDESRKLNRIYKFQGK 190                   210                   230
AWDWEVSNENGNYDYLTYADIDYDHPDVAAEIKRWGTWYANELQLDGFRLDAVKHIKFSF 250                   270                   290
LRDWVNHVREKTGKEMFTVAEYWQNDLGALENYLNKTNFNHSVFDVPLHYQFHAASTQGG 310                   330                   350
GYDMRKLLNGTVVSKHPLKSVTFVDNHDTQPGQSLESTVQTWFKPLAYAFILTRESGYPQ 370                   390                   410
VFYGDMYGTKGDSQREIPALKHKIEPILKARKQYAYGAQHDYFDHHDIVGWTREGDSSVA 430                   450                   470
NSGLAALITDGPGGAKRMYVGRQNAGETWHDITGNRSEPVVINSEGWGEFHVNGGSVSIY

VQR
```

FIG._4a

```
                                                                AAAA
         14                  34                   54
ANLNGTLMQYFEWYMPNDGQHWKRLQNDSAYLAEHGITAVWIPPAYKGTSQADVGYGAYD 74                  94                  114
LYDLGEFHQKGTVRTKYGTKGELQSAIKSLHSRDINVYGDVVINHKGGADATEDVTAVEV 134                 154                 174
DPADRNRVISGEHLIKAWTHFHFPGRGSTYSDFKWHWYHFDGTDWDESRKLNRIYKFQGK 194                 214                 234
AWDWEVSNENGNYDYLMYADIDYDHPDVAAEIKRWGTWYANELQLDGFRLDAVKHIKFSF 254                 274                 294
LRDWVNHVREKTGKEMFTVAEYWQNDLGALENYLNKTNFNHSVFDVPLHYQFHAASTQGG 314                 334                 354
GYDMRKLLNGTVVSKHPLKSVTFVDNHDTQPGQSLESTVQTWFKPLAYAFILTRESGYPQ 374                 394                 414
VFYGDMYGTKGDSQREIPALKHKIEPILKARKQYAYGAQHDYFDHHDIVGWTREGDSSVA 434                 454                 474
NSGLAALITDGPGGAKRMYVGRQNAGETWHDITGNRSEPVVINSEGWGEFHVNGGSVSIY

VQR
```

FIG._4b

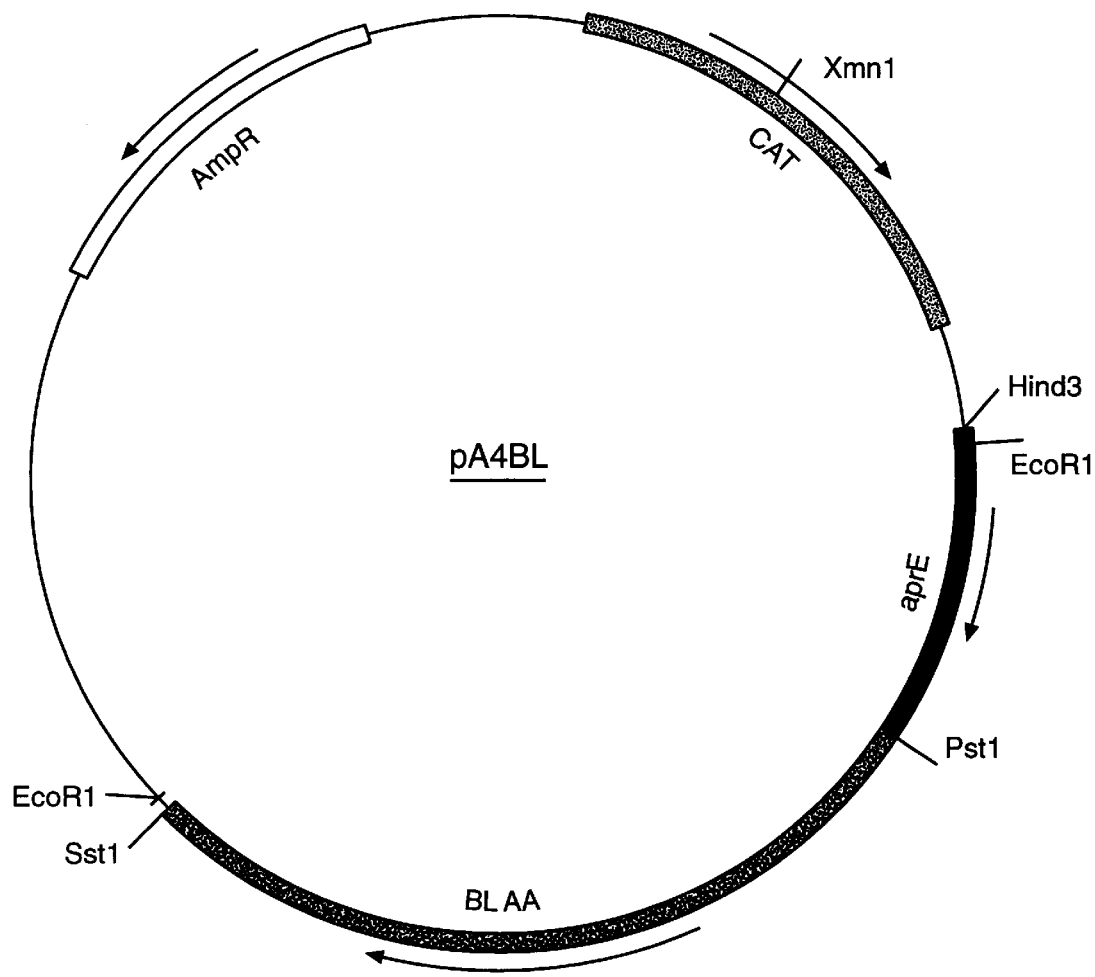
FIG._5

SIGNAL SEQUENCE - MATURE PROTEIN JUNCTIONS IN:

*B.licheniformis* alpha-amylase.                               (PstI)

M K Q Q K R L T A R L L T L L F A L I F L L P H S A A A A [A N L ......

N-terminus

*B.subtilis* alkaline protease aprE.                        (PstI)

M R S K T L W I S L L F A L T L I F T M A F S N M S A Q A [A G K S ......

N-terminus

*B.licheniformis* alpha-amylase in pA4BL.           (PstI)

M R S K T L W I S L L F A L T L I F T M A F S N M S A Q A [A A A A N.

N-terminus

*B.lichenfiormis* alpha-amylase in pBLapr.

M R S K T L W I S L L F A L T L I F T M A F S N M S A Q A [A N L ......

N-terminus (PstI) ↓ indicates the site of the restriction site in the gene.

N-terminus indicates cleavage site between signal peptide and secreted protein.

FIG._6

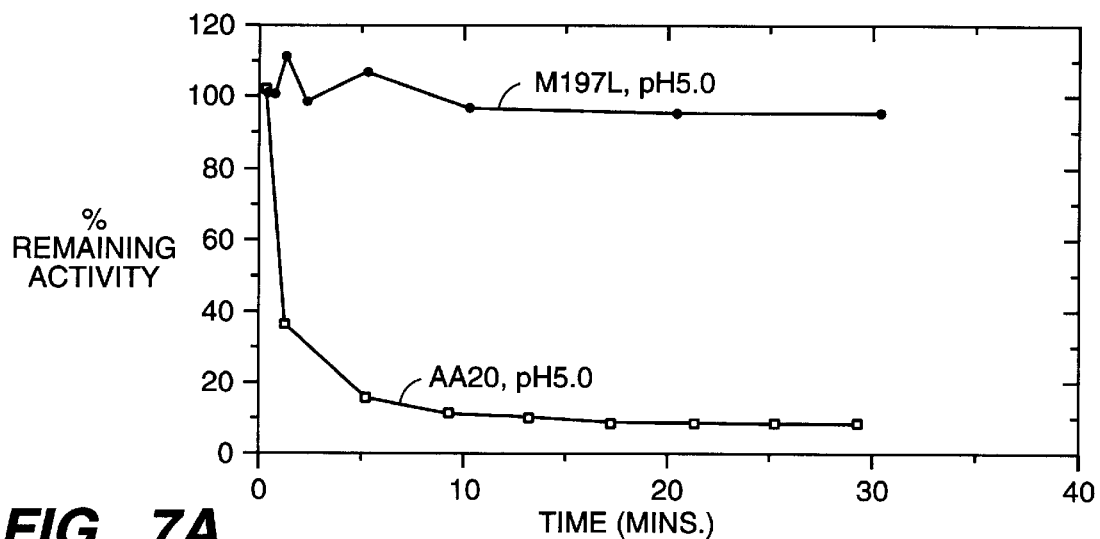
FIG._7A
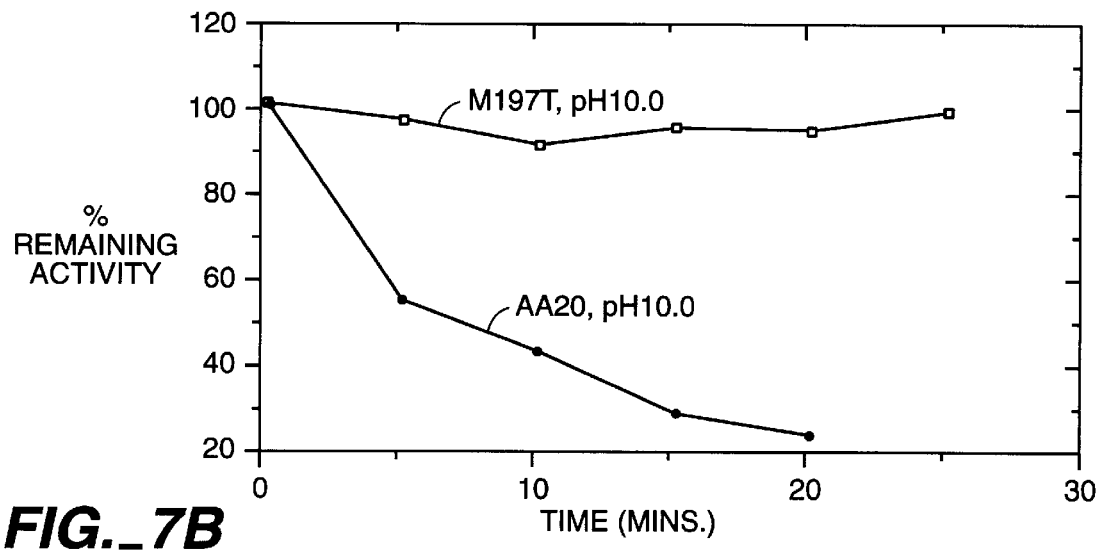
FIG._7B
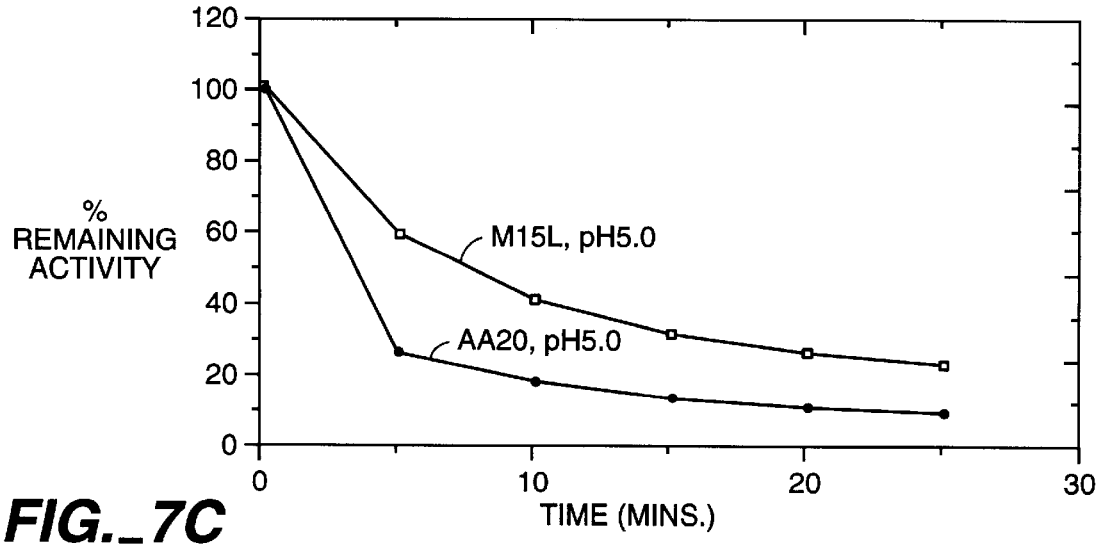
FIG._7C

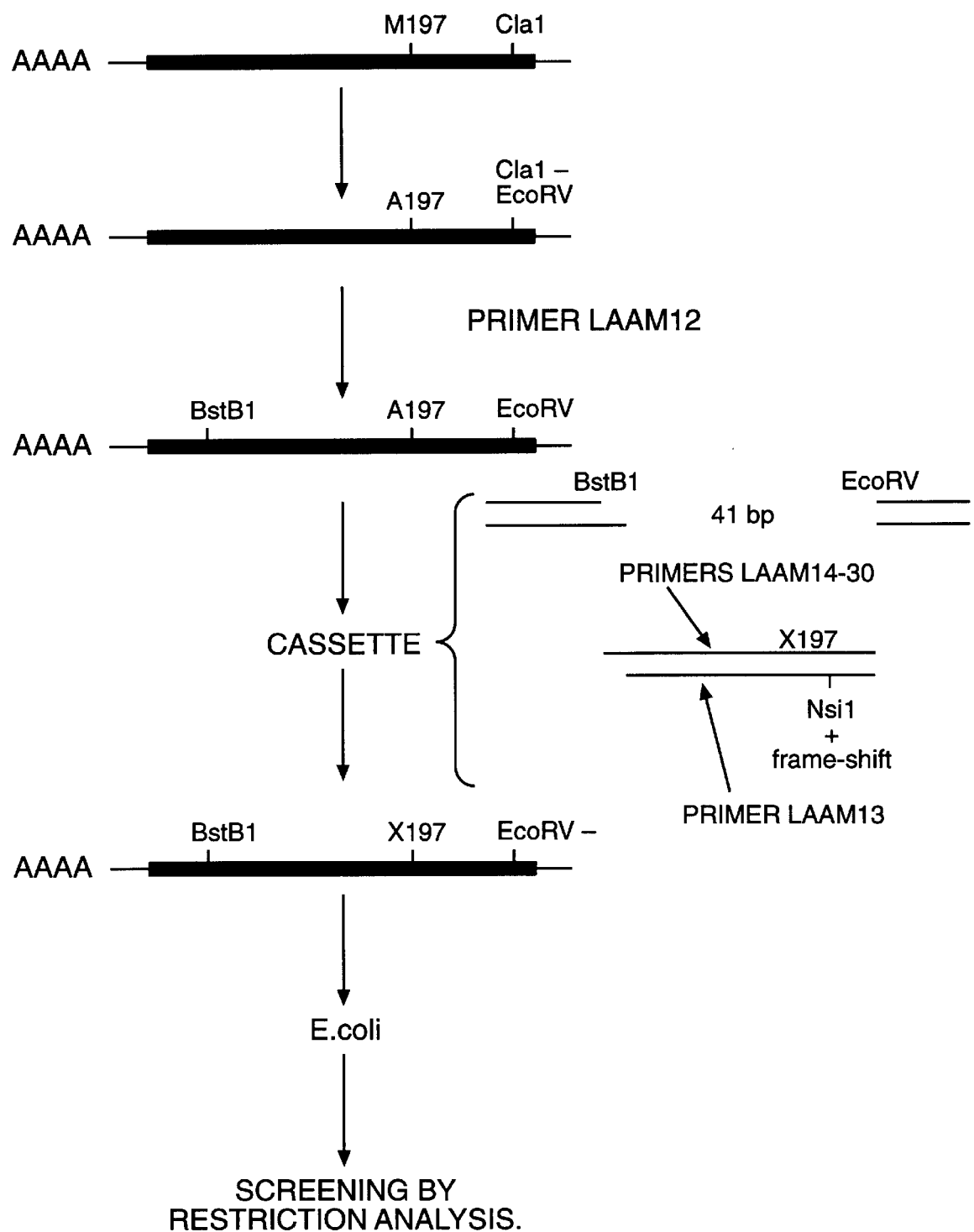
FIG._8

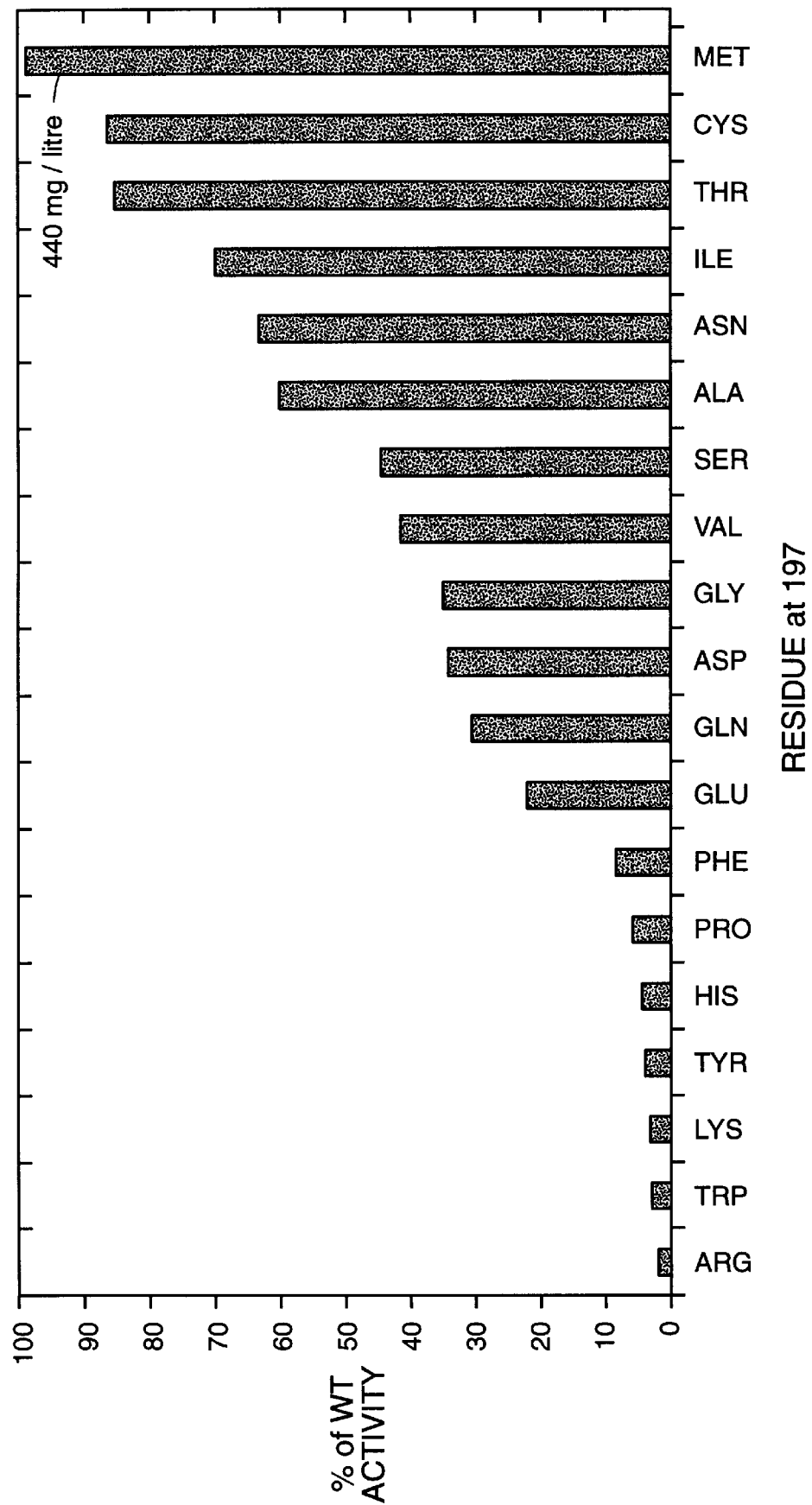
FIG._9

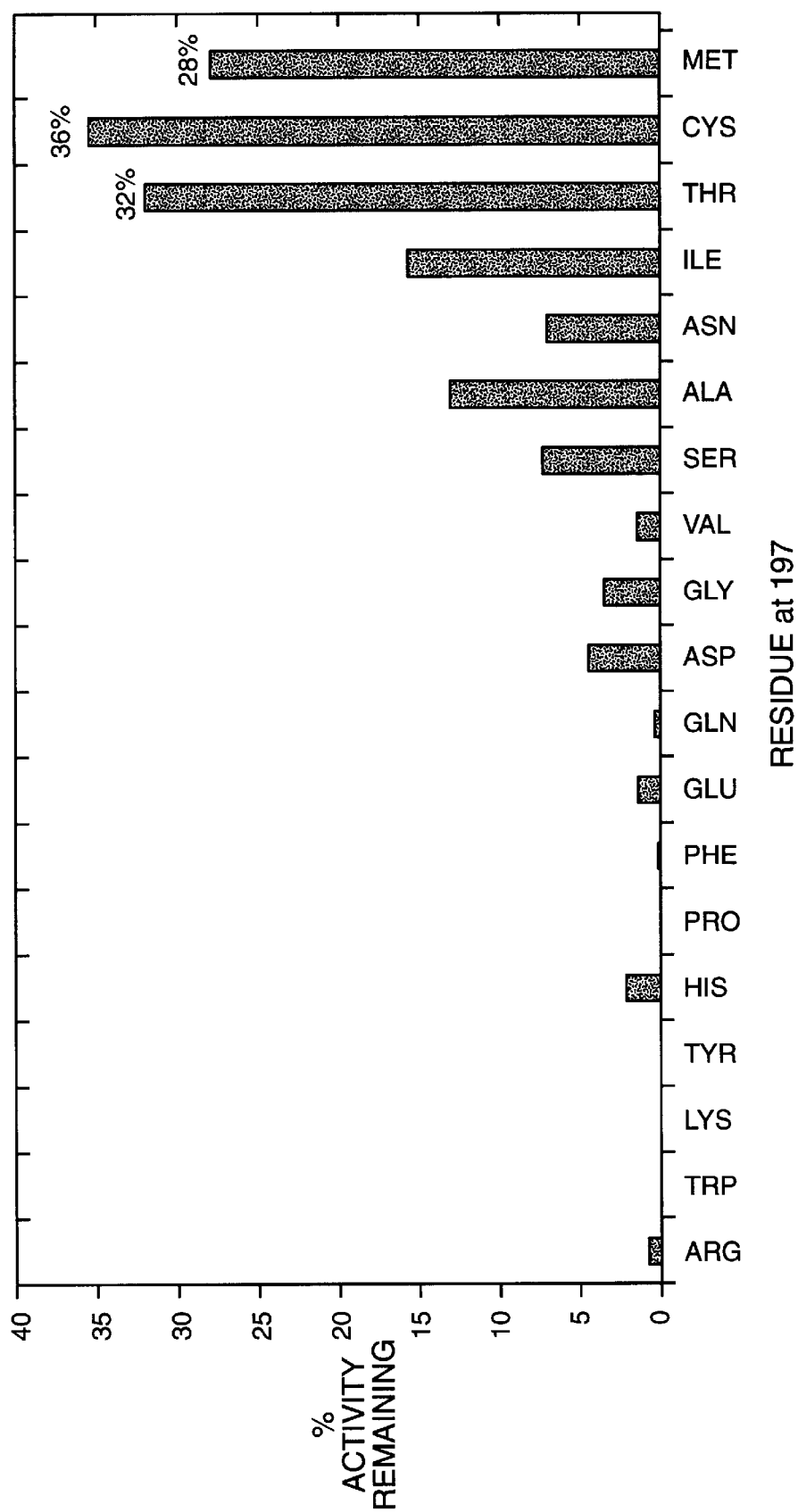
FIG._10

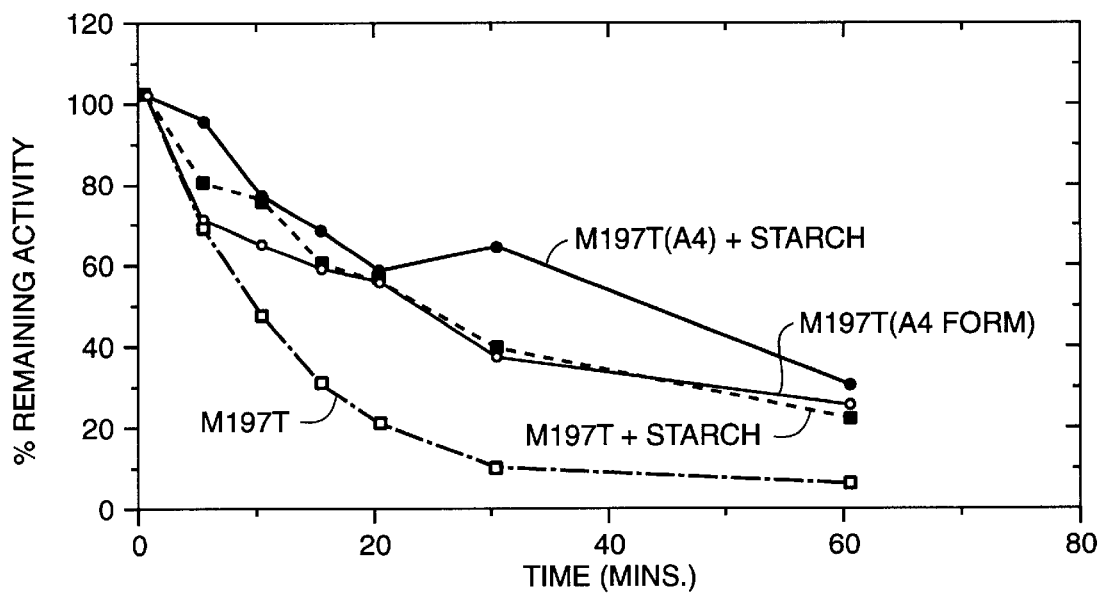
FIG._11A
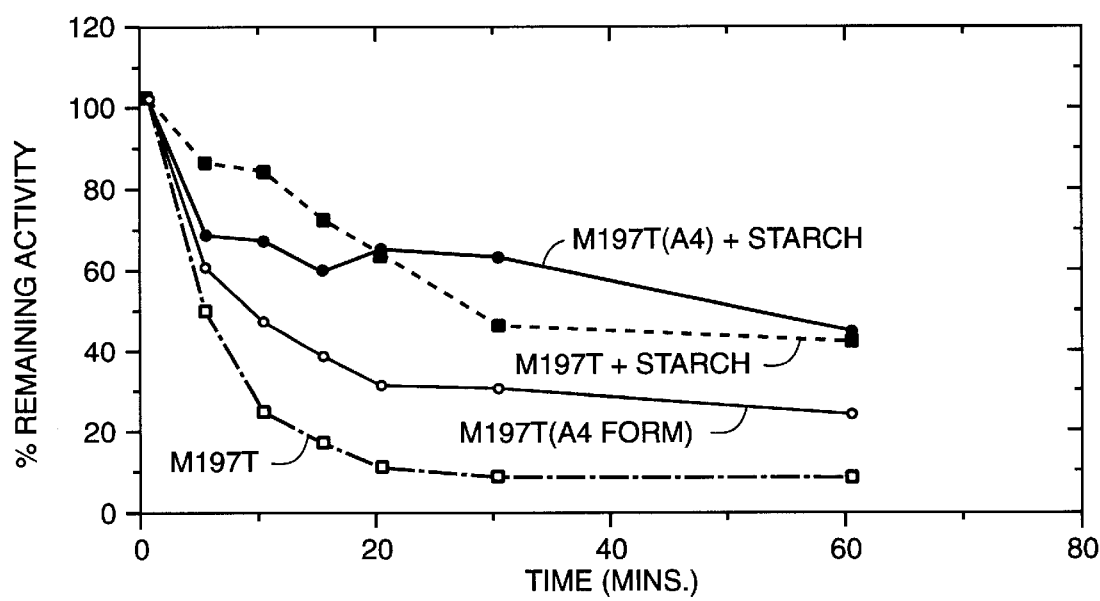
FIG._11B

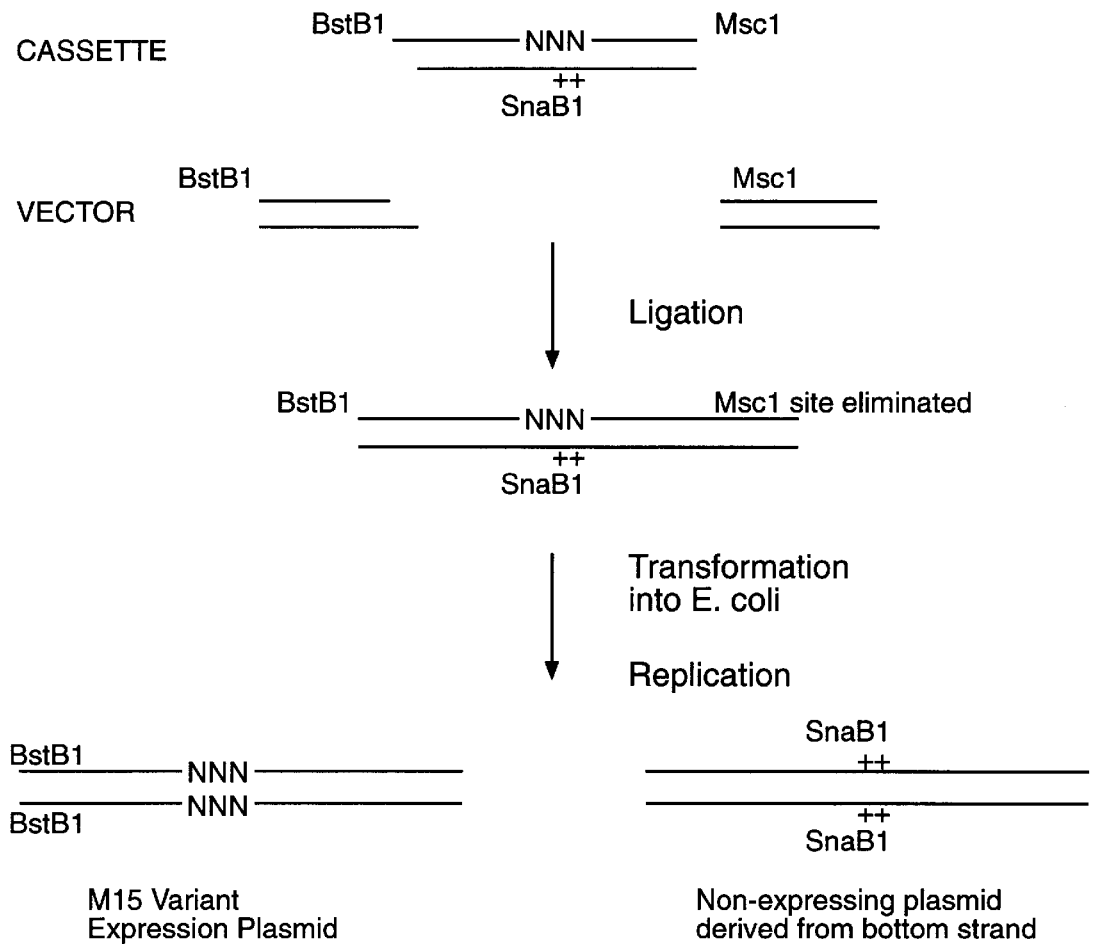
FIG._12

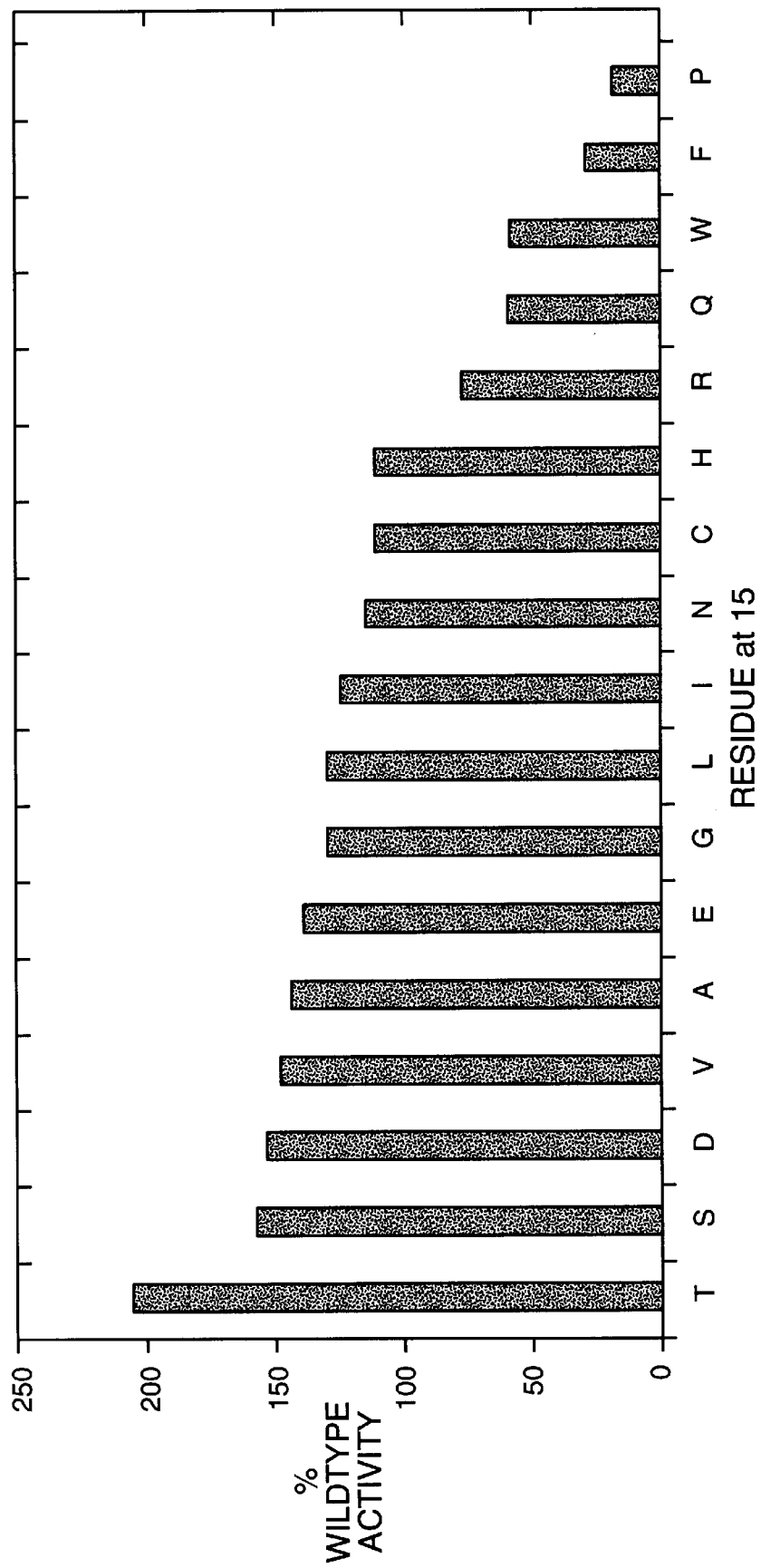
FIG._13

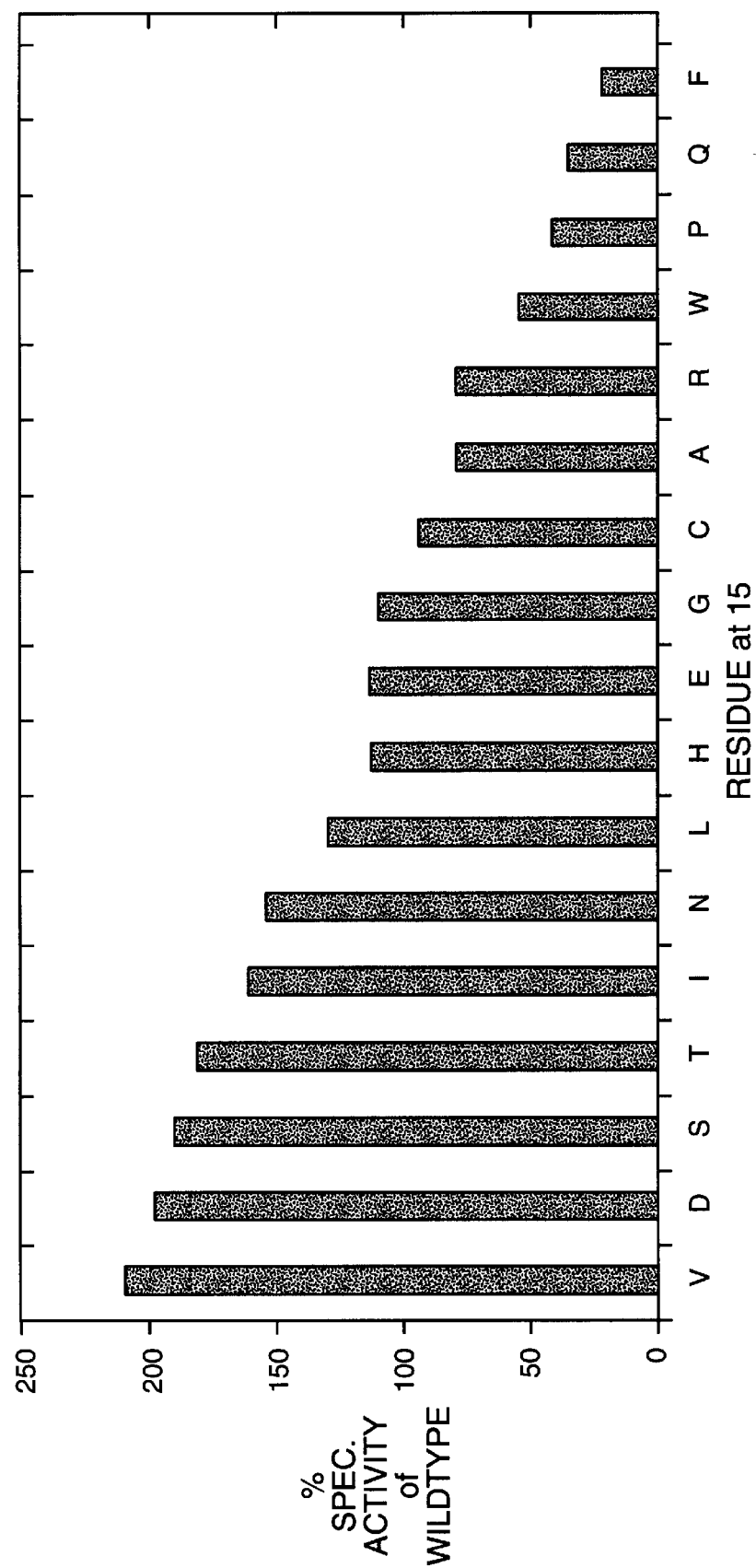
FIG._14

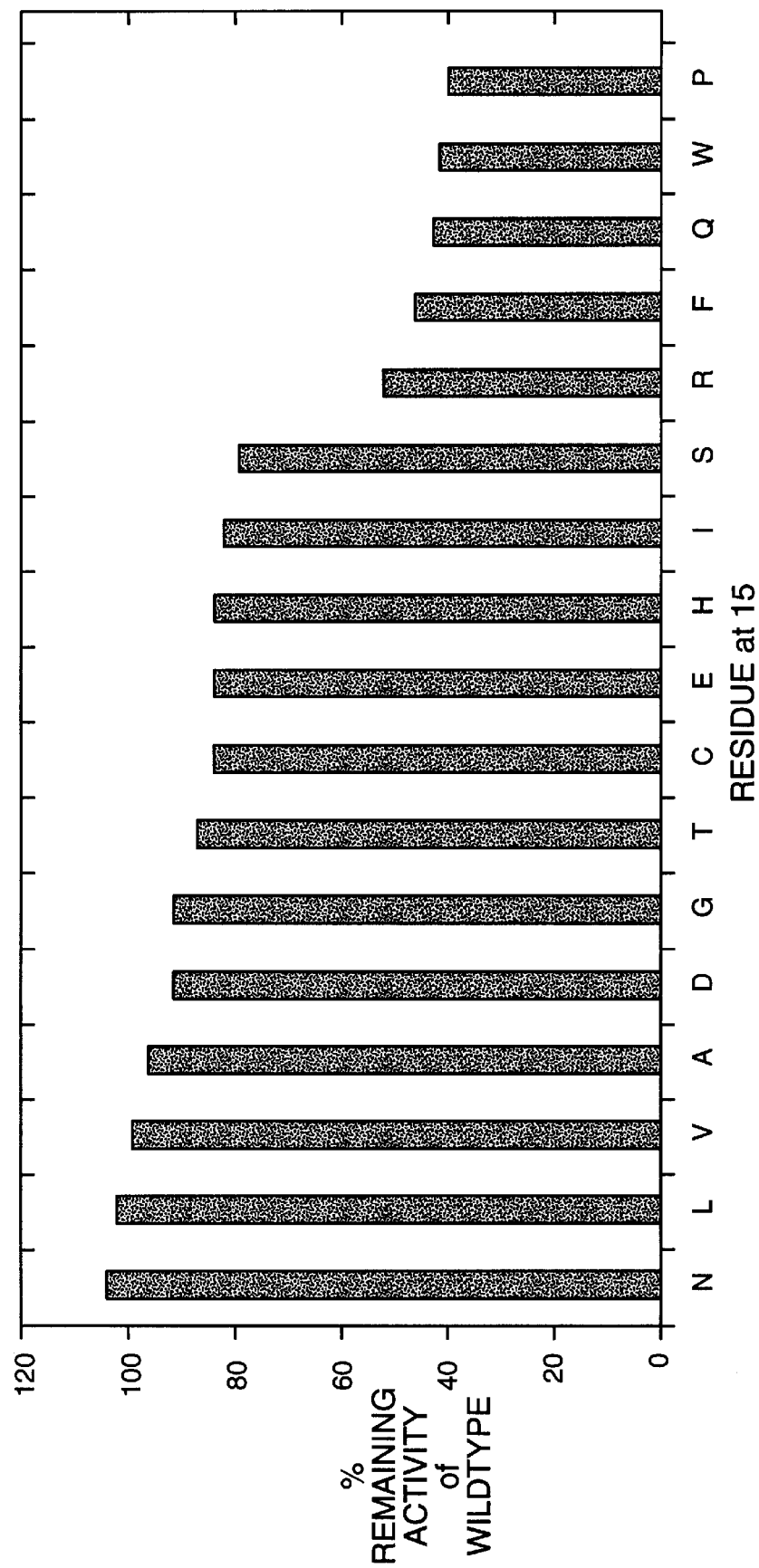
FIG._15

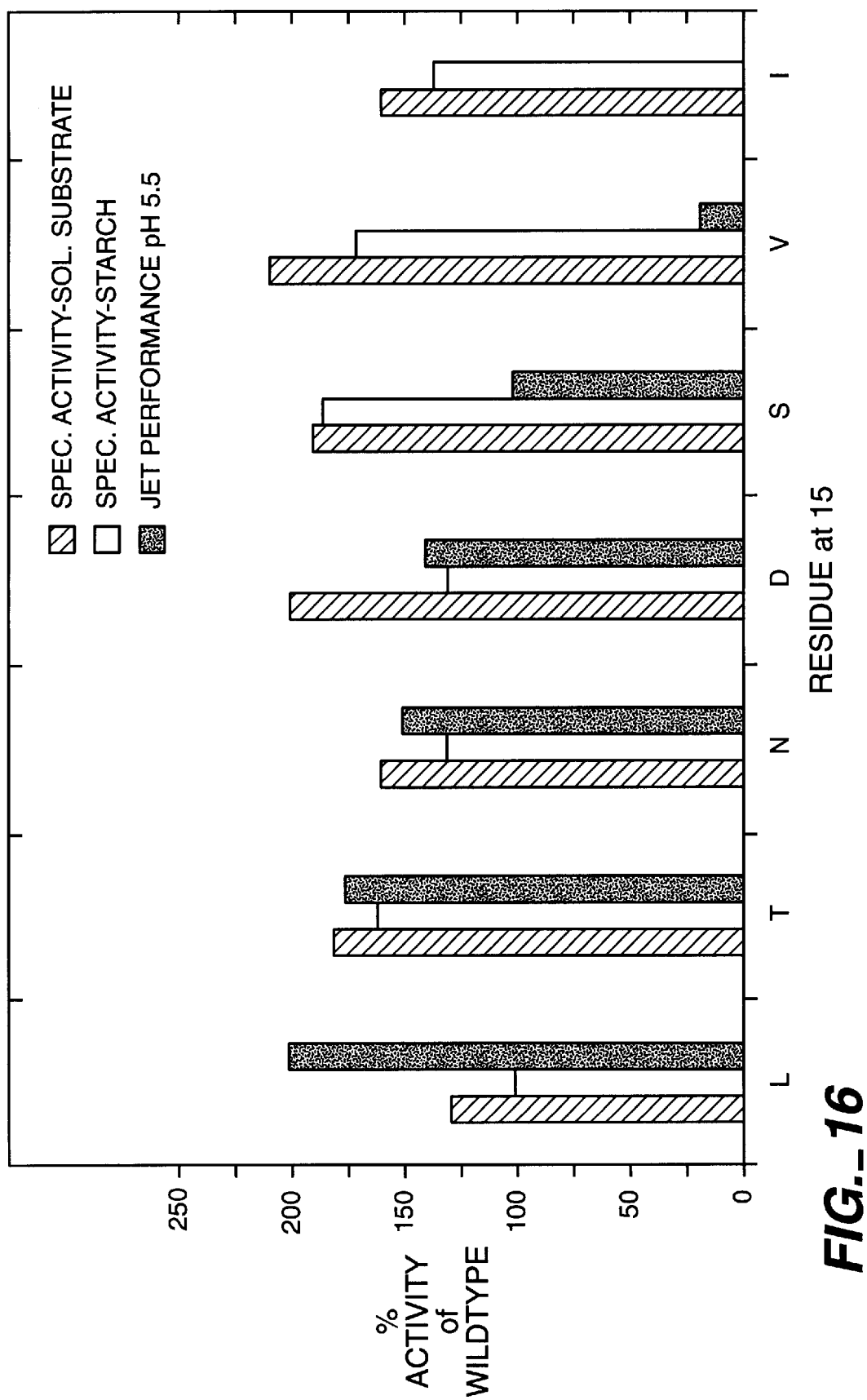
FIG._16

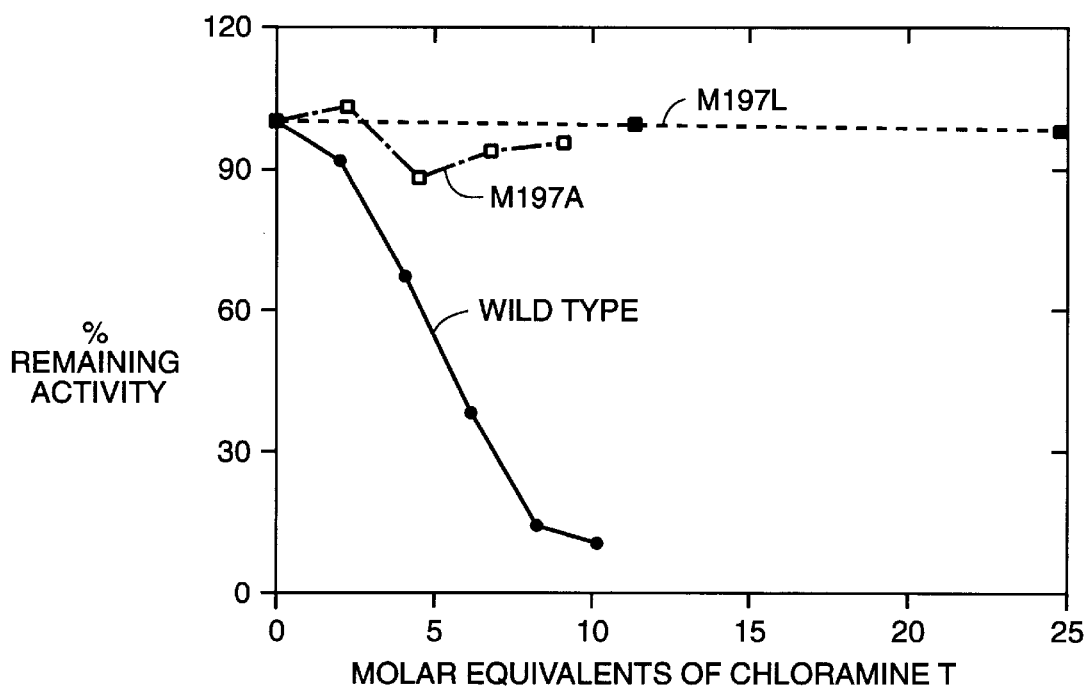
FIG._17
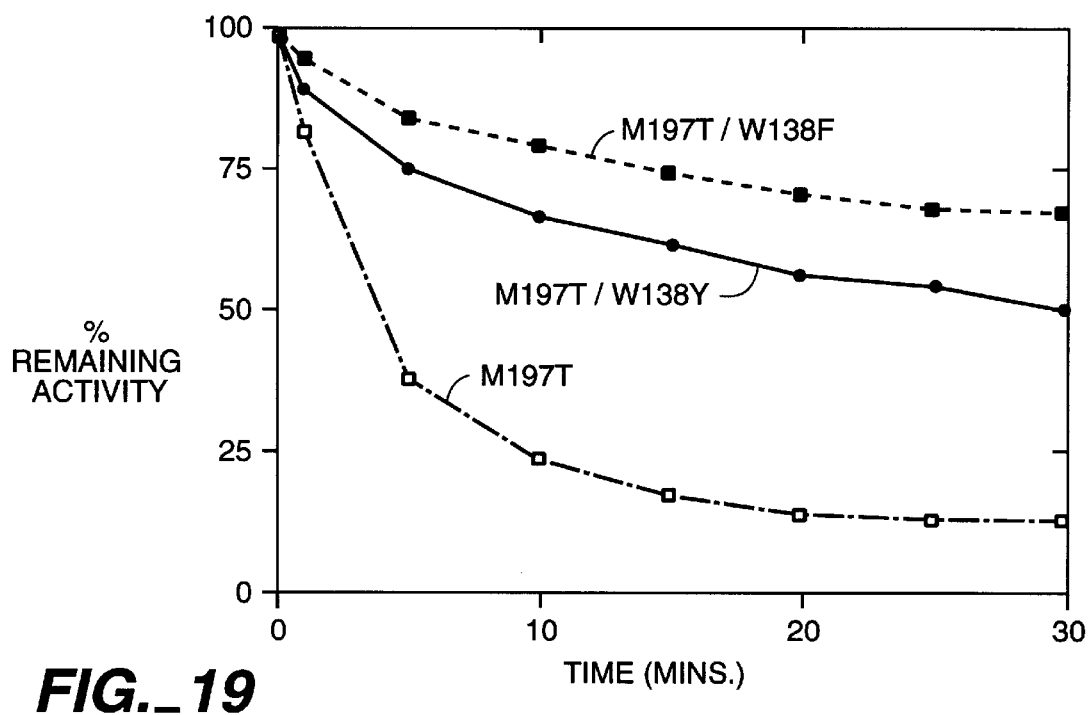
FIG._19

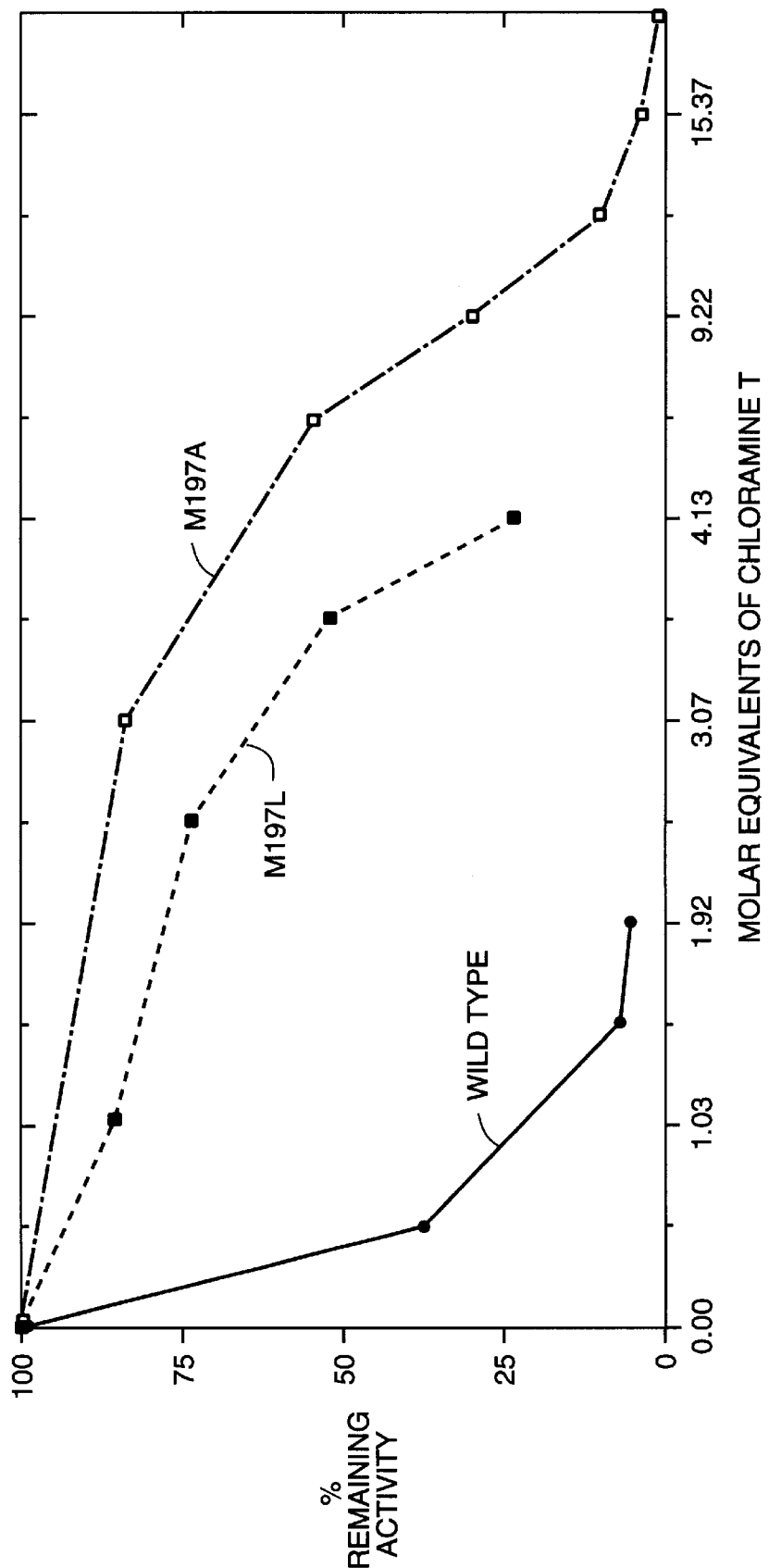
FIG._18

SEQUENCE LISTING ( 1 ) GENERAL INFORMATION:

( i i i ) NUMBER OF SEQUENCES: 68

( 2 ) INFORMATION FOR SEQ ID NO:1:

( i ) SEQUENCE CHARACTERISTICS:
( A ) LENGTH: 56 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:1:

GATCAAAACA TAAAAAACCG GCCTTGGCCC CGCCGGTTTT TTATTATTTT TGAGCT 56

( 2 ) INFORMATION FOR SEQ ID NO:2:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:2:

TGGGACGCTG GCGCAGTACT TTGAATGGT 29

( 2 ) INFORMATION FOR SEQ ID NO:3:

( i ) SEQUENCE CHARACTERISTICS:
( A ) LENGTH: 34 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:3:

TGATGCAGTA CTTTGAATGG TACCTGCCCA ATGA 34

( 2 ) INFORMATION FOR SEQ ID NO:4:

( i ) SEQUENCE CHARACTERISTICS:
( A ) LENGTH: 36 base pairs
( B ) TYPE: nucleic acid
( C ) STRANDEDNESS: single
( D ) TOPOLOGY: linear ( i i ) MOLECULE TYPE: DNA (genomic)

( x i ) SEQUENCE DESCRIPTION: SEQ ID NO:4:

GATTATTTGT TGTATGCCGA TATCGACTAT GACCAT 36

( 2 ) INFORMATION FOR SEQ ID NO:5:

( i ) SEQUENCE CHARACTERISTICS:
          ( A ) LENGTH: 26 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:5:

CGGGGAAGGA GGCCTTTACG GTAGCT     26

( 2 ) INFORMATION FOR SEQ ID NO:6:

( i ) SEQUENCE CHARACTERISTICS:
          ( A ) LENGTH: 24 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:6:

GCGGCTATGA CTTAAGGAAA TTGC     24

( 2 ) INFORMATION FOR SEQ ID NO:7:

( i ) SEQUENCE CHARACTERISTICS:
          ( A ) LENGTH: 23 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:7:

CTACGGGGAT GCATACGGGA CGA     23

( 2 ) INFORMATION FOR SEQ ID NO:8:

( i ) SEQUENCE CHARACTERISTICS:
          ( A ) LENGTH: 35 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:8:

CTACGGGGAT TACTACGGGA CCAAGGGAGA CTCCC     35

( 2 ) INFORMATION FOR SEQ ID NO:9:

( i ) SEQUENCE CHARACTERISTICS:
          ( A ) LENGTH: 36 base pairs
          ( B ) TYPE: nucleic acid
          ( C ) STRANDEDNESS: single
          ( D ) TOPOLOGY: linear ( i i ) MOLECULE TYPE: DNA (genomic)

( x i ) SEQUENCE DESCRIPTION: SEQ ID NO:9:

CCGGTGGGGC CAAGCGGGCC TATGTTGGCC GGCAAA     36

( 2 ) INFORMATION FOR SEQ ID NO:10:

( i ) SEQUENCE CHARACTERISTICS:
          ( A ) LENGTH: 45 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:10:

CATCAGCGTC CCATTAAGAT TTGCAGCCTG CGCAGACATG TTGCT    45

(2) INFORMATION FOR SEQ ID NO:11:

(i) SEQUENCE CHARACTERISTICS:
(A) LENGTH: 36 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:11:

GATTATTTGG CGTATGCCGA TATCGACTAT GACCAT    36

(2) INFORMATION FOR SEQ ID NO:12:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:12:

GGGAAGTTTC GAATGAAAAC G    21

(2) INFORMATION FOR SEQ ID NO:13:

(i) SEQUENCE CHARACTERISTICS:
(A) LENGTH: 38 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:13:

GTCGGCATAT GCATATAATC ATAGTTGCCG TTTTCATT    38

(2) INFORMATION FOR SEQ ID NO:14:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:14:

CGAATGAAAA CGGCAACTAT GATTATTTGA TCTATGCCGA C    41

(2) INFORMATION FOR SEQ ID NO:15:

(i) SEQUENCE CHARACTERISTICS:
(A) LENGTH: 41 base pairs
(B) TYPE: nucleic acid
(C) STRANDEDNESS: single
(D) TOPOLOGY: linear (ii) MOLECULE TYPE: DNA (genomic)

( x i ) SEQUENCE DESCRIPTION: SEQ ID NO:15:

CGAATGAAAA CGGCAACTAT GATTATTTGT TCTATGCCGA C          41

( 2 ) INFORMATION FOR SEQ ID NO:16:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:16:

CGAATGAAAA CGGCAACTAT GATTATTTGG TTTATGCCGA C          41

( 2 ) INFORMATION FOR SEQ ID NO:17:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:17:

CGAATGAAAA CGGCAACTAT GATTATTTGA GCTATGCCGA C          41

( 2 ) INFORMATION FOR SEQ ID NO:18:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:18:

CGAATGAAAA CGGCAACTAT GATTATTTGC CTTATGCCGA C          41

( 2 ) INFORMATION FOR SEQ ID NO:19:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:19:

CGAATGAAAA CGGCAACTAT GATTATTTGA CATATGCCGA C          41

( 2 ) INFORMATION FOR SEQ ID NO:20:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:20:

CGAATGAAAA CGGCAACTAT GATTATTTGT ACTATGCCGA C          41

(2) INFORMATION FOR SEQ ID NO:21:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

CGAATGAAAA CGGCAACTAT GATTATTTGC ACTATGCCGA C      41

(2) INFORMATION FOR SEQ ID NO:22:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

CGAATGAAAA CGGCAACTAT GATTATTTGG GCTATGCCGA C      41

(2) INFORMATION FOR SEQ ID NO:23:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

CGAATGAAAA CGGCAACTAT GATTATTTGC AATATGCCGA C      41

(2) INFORMATION FOR SEQ ID NO:24:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

CGAATGAAAA CGGCAACTAT GATTATTTGA ACTATGCCGA C      41

(2) INFORMATION FOR SEQ ID NO:25:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:25:

GCAATGAAAA CGGCAACTAT GATTATTTGA AATATGCCGA C      41

(2) INFORMATION FOR SEQ ID NO:26:

(i) SEQUENCE CHARACTERISTICS:
        (A) LENGTH: 41 base pairs ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:26:

CGAATGAAAA CGGCAACTAT GATTATTTGG ATTATGCCGA C     41

( 2 ) INFORMATION FOR SEQ ID NO:27:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:27:

CGAATGAAAA CGGCAACTAT GATTATTTGG AATATGCCGA C     41

( 2 ) INFORMATION FOR SEQ ID NO:28:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:28:

CGAATGAAAA CGGCAACTAT GATTATTTGT GTATTGCCGA C     41

( 2 ) INFORMATION FOR SEQ ID NO:29:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:29:

CGAATGAAAA CGGCAACTAT GATTATTTGT GGTATGCCGA C     41

( 2 ) INFORMATION FOR SEQ ID NO:30:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:30:

CGAATGAAAA CGGCAACTAT GATTATTTGA GATATGCCGA C     41

( 2 ) INFORMATION FOR SEQ ID NO:31:

( i ) SEQUENCE CHARACTERISTICS:
        ( A ) LENGTH: 1968 base pairs
        ( B ) TYPE: nucleic acid
        ( C ) STRANDEDNESS: single
        ( D ) TOPOLOGY: linear ( i i ) MOLECULE TYPE: DNA (genomic)

(x i) SEQUENCE DESCRIPTION: SEQ ID NO:31:

| | | | | | | |
|---|---|---|---|---|---|---|
| AGCTTGAAGA | AGTGAAGAAG | CAGAGAGGCT | ATTGAATAAA | TGAGTAGAAA | GCGCCATATC | 60 |
| GGCGCTTTTC | TTTTGGAAGA | AAATATAGGG | AAAATGGTAC | TTGTTAAAAA | TTCGGAATAT | 120 |
| TTATACAACA | TCATATGTTT | CACATTGAAA | GGGGAGGAGA | ATCATGAAAC | AACAAAAACG | 180 |
| GCTTTACGCC | CGATTGCTGA | CGCTGTTATT | TGCGCTCATC | TTCTTGCTGC | CTCATTCTGC | 240 |
| AGCAGCGGCG | GCAAATCTTA | ATGGGACGCT | GATGCAGTAT | TTTGAATGGT | ACATGCCCAA | 300 |
| TGACGGCCAA | CATTGGAAGC | GTTTGCAAAA | CGACTCGGCA | TATTTGGCTG | AACACGGTAT | 360 |
| TACTGCCGTC | TGGATTCCCC | CGGCATATAA | GGGAACGAGC | CAAGCGGATG | TGGGCTACGG | 420 |
| TGCTTACGAC | CTTTATGATT | TAGGGGAGTT | TCATCAAAAA | GGGACGGTTC | GGACAAAGTA | 480 |
| CGGCACAAAA | GGAGAGCTGC | AATCTGCGAT | CAAAAGTCTT | CATTCCCGCG | ACATTAACGT | 540 |
| TTACGGGGAT | GTGGTCATCA | ACCACAAAGG | CGGCGCTGAT | GCGACCGAAG | ATGTAACCGC | 600 |
| GGTTGAAGTC | GATCCCGCTG | ACCGCAACCG | CGTAATTTCA | GGAGAACACC | TAATTAAAGC | 660 |
| CTGGACACAT | TTTCATTTTC | CGGGGCGCGG | CAGCACATAC | AGCGATTTTA | AATGGCATTG | 720 |
| GTACCATTTT | GACGGAACCG | ATTGGGACGA | GTCCCGAAAG | CTGAACCGCA | TCTATAAGTT | 780 |
| TCAAGGAAAG | GCTTGGGATT | GGGAAGTTTC | CAATGAAAAC | GGCAACTATG | ATTATTTGAT | 840 |
| GTATGCCGAC | ATCGATTATG | ACCATCCTGA | TGTCGCAGCA | GAAATTAAGA | GATGGGGCAC | 900 |
| TTGGTATGCC | AATGAACTGC | AATTGGACGG | TTTCCGTCTT | GATGCTGTCA | AACACATTAA | 960 |
| ATTTTCTTTT | TTGCGGGATT | GGGTTAATCA | TGTCAGGGAA | AAAACGGGGA | AGGAAATGTT | 1020 |
| TACGGTAGCT | GAATATTGGC | AGAATGACTT | GGGCGCGCTG | GAAAACTATT | TGAACAAAAC | 1080 |
| AAATTTTAAT | CATTCAGTGT | TTGACGTGCC | GCTTCATTAT | CAGTTCCATG | CTGCATCGAC | 1140 |
| ACAGGGAGGC | GGCTATGATA | TGAGGAAATT | GCTGAACGGT | ACGGTCGTTT | CCAAGCATCC | 1200 |
| GTTGAAATCG | GTTACATTTG | TCGATAACCA | TGATACACAG | CCGGGGCAAT | CGCTTGAGTC | 1260 |
| GACTGTCCAA | ACATGGTTTA | AGCCGCTTGC | TTACGCTTTT | ATTCTCACAA | GGGAATCTGG | 1320 |
| ATACCCTCAG | GTTTTCTACG | GGGATATGTA | CGGGACGAAA | GGAGACTCCC | AGCGCGAAAT | 1380 |
| TCCTGCCTTG | AAACACAAAA | TTGAACCGAT | CTTAAAAGCG | AGAAAACAGT | ATGCGTACGG | 1440 |
| AGCACAGCAT | GATTATTTCG | ACCACCATGA | CATTGTCGGC | TGGACAAGGG | AAGGCGACAG | 1500 |
| CTCGGTTGCA | AATTCAGGTT | TGGCGGCATT | AATAACAGAC | GGACCCGGTG | GGGCAAAGCG | 1560 |
| AATGTATGTC | GGCCGGCAAA | ACGCCGGTGA | GACATGGCAT | GACATTACCG | GAAACCGTTC | 1620 |
| GGAGCCGGTT | GTCATCAATT | CGGAAGGCTG | GGGAGAGTTT | CACGTAAACG | GCGGGTCGGT | 1680 |
| TTCAATTTAT | GTTCAAAGAT | AGAAGAGCAG | AGAGGACGGA | TTTCCTGAAG | GAAATCCGTT | 1740 |
| TTTTTATTTT | GCCCGTCTTA | TAAATTTCTT | TGATTACATT | TTATAATTAA | TTTTAACAAA | 1800 |
| GTGTCATCAG | CCCTCAGGAA | GGACTTGCTG | ACAGTTTGAA | TCGCATAGGT | AAGGCGGGGA | 1860 |
| TGAAATGGCA | ACGTTATCTG | ATGTAGCAAA | GAAAGCAAAT | GTGTCGAAAA | TGACGGTATC | 1920 |
| GCGGGTGATC | AATCATCCTG | AGACTGTGAC | GGATGAATTG | AAAAAGCT | | 1968 |

(2) INFORMATION FOR SEQ ID NO:32:

(i) SEQUENCE CHARACTERISTICS:
        (A) LENGTH: 483 amino acids
        (B) TYPE: amino acid
        (C) STRANDEDNESS: single
        (D) TOPOLOGY: linear (ii) MOLECULE TYPE: protein ( x i ) SEQUENCE DESCRIPTION: SEQ ID NO:32:

| Ala | Asn | Leu | Asn | Gly | Thr | Leu | Met | Gln | Tyr | Phe | Glu | Trp | Tyr | Met | Pro |
|---|---|---|---|---|---|---|---|---|---|---|---|---|---|---|---|
| 1 | | | | 5 | | | | | 10 | | | | | 15 | |

| Asn | Asp | Gly | Gln | His | Trp | Lys | Arg | Leu | Gln | Asn | Asp | Ser | Ala | Tyr | Leu |
|---|---|---|---|---|---|---|---|---|---|---|---|---|---|---|---|
| | | | 20 | | | | 25 | | | | | 30 | | | |

| Ala | Glu | His | Gly | Ile | Thr | Ala | Val | Trp | Ile | Pro | Pro | Ala | Tyr | Lys | Gly |
|---|---|---|---|---|---|---|---|---|---|---|---|---|---|---|---|
| | | 35 | | | | | 40 | | | | | 45 | | | |

| Thr | Ser | Gln | Ala | Asp | Val | Gly | Tyr | Gly | Ala | Tyr | Asp | Leu | Tyr | Asp | Leu |
|---|---|---|---|---|---|---|---|---|---|---|---|---|---|---|---|
| | 50 | | | | | 55 | | | | | | 60 | | | |

| Gly | Glu | Phe | His | Gln | Lys | Gly | Thr | Val | Arg | Thr | Lys | Tyr | Gly | Thr | Lys |
|---|---|---|---|---|---|---|---|---|---|---|---|---|---|---|---|
| 65 | | | | | 70 | | | | | 75 | | | | | 80 |

| Gly | Glu | Leu | Gln | Ser | Ala | Ile | Lys | Ser | Leu | His | Ser | Arg | Asp | Ile | Asn |
|---|---|---|---|---|---|---|---|---|---|---|---|---|---|---|---|
| | | | | 85 | | | | | 90 | | | | | 95 | |

| Val | Tyr | Gly | Asp | Val | Val | Ile | Asn | His | Lys | Gly | Gly | Ala | Asp | Ala | Thr |
|---|---|---|---|---|---|---|---|---|---|---|---|---|---|---|---|
| | | | 100 | | | | 105 | | | | | 110 | | | |

| Glu | Asp | Val | Thr | Ala | Val | Glu | Val | Asp | Pro | Ala | Asp | Arg | Asn | Arg | Val |
|---|---|---|---|---|---|---|---|---|---|---|---|---|---|---|---|
| | | | 115 | | | | 120 | | | | | 125 | | | |

| Ile | Ser | Gly | Glu | His | Leu | Ile | Lys | Ala | Trp | Thr | His | Phe | His | Phe | Pro |
|---|---|---|---|---|---|---|---|---|---|---|---|---|---|---|---|
| | | 130 | | | | | 135 | | | | | 140 | | | |

| Gly | Arg | Gly | Ser | Thr | Tyr | Ser | Asp | Phe | Lys | Trp | His | Trp | Tyr | His | Phe |
|---|---|---|---|---|---|---|---|---|---|---|---|---|---|---|---|
| 145 | | | | | 150 | | | | | 155 | | | | | 160 |

| Asp | Gly | Thr | Asp | Trp | Asp | Glu | Ser | Arg | Lys | Leu | Asn | Arg | Ile | Tyr | Lys |
|---|---|---|---|---|---|---|---|---|---|---|---|---|---|---|---|
| | | | | 165 | | | | | 170 | | | | | 175 | |

| Phe | Gln | Gly | Lys | Ala | Trp | Asp | Trp | Glu | Val | Ser | Asn | Glu | Asn | Gly | Asn |
|---|---|---|---|---|---|---|---|---|---|---|---|---|---|---|---|
| | | | 180 | | | | 185 | | | | | 190 | | | |

| Tyr | Asp | Tyr | Leu | Met | Tyr | Ala | Asp | Ile | Asp | Tyr | Asp | His | Pro | Asp | Val |
|---|---|---|---|---|---|---|---|---|---|---|---|---|---|---|---|
| | | 195 | | | | | 200 | | | | | 205 | | | |

| Ala | Ala | Glu | Ile | Lys | Arg | Trp | Gly | Thr | Trp | Tyr | Ala | Asn | Glu | Leu | Gln |
|---|---|---|---|---|---|---|---|---|---|---|---|---|---|---|---|
| | 210 | | | | | 215 | | | | | 220 | | | | |

| Leu | Asp | Gly | Phe | Arg | Leu | Asp | Ala | Val | Lys | His | Ile | Lys | Phe | Ser | Phe |
|---|---|---|---|---|---|---|---|---|---|---|---|---|---|---|---|
| 225 | | | | | 230 | | | | | 235 | | | | | 240 |

| Leu | Arg | Asp | Trp | Val | Asn | His | Val | Arg | Glu | Lys | Thr | Gly | Lys | Glu | Met |
|---|---|---|---|---|---|---|---|---|---|---|---|---|---|---|---|
| | | | | 245 | | | | | 250 | | | | | 255 | |

| Phe | Thr | Val | Ala | Glu | Tyr | Trp | Gln | Asn | Asp | Leu | Gly | Ala | Leu | Glu | Asn |
|---|---|---|---|---|---|---|---|---|---|---|---|---|---|---|---|
| | | | 260 | | | | 265 | | | | | 270 | | | |

| Tyr | Leu | Asn | Lys | Thr | Asn | Phe | Asn | His | Ser | Val | Phe | Asp | Val | Pro | Leu |
|---|---|---|---|---|---|---|---|---|---|---|---|---|---|---|---|
| | | 275 | | | | | 280 | | | | | 285 | | | |

| His | Tyr | Gln | Phe | His | Ala | Ala | Ser | Thr | Gln | Gly | Gly | Gly | Tyr | Asp | Met |
|---|---|---|---|---|---|---|---|---|---|---|---|---|---|---|---|
| | 290 | | | | | 295 | | | | | 300 | | | | |

| Arg | Lys | Leu | Leu | Asn | Gly | Thr | Val | Val | Ser | Lys | His | Pro | Leu | Lys | Ser |
|---|---|---|---|---|---|---|---|---|---|---|---|---|---|---|---|
| 305 | | | | | 310 | | | | | 315 | | | | | 320 |

| Val | Thr | Phe | Val | Asp | Asn | His | Asp | Thr | Gln | Pro | Gly | Gln | Ser | Leu | Glu |
|---|---|---|---|---|---|---|---|---|---|---|---|---|---|---|---|
| | | | | 325 | | | | | 330 | | | | | 335 | |

| Ser | Thr | Val | Gln | Thr | Trp | Phe | Lys | Pro | Leu | Ala | Tyr | Ala | Phe | Ile | Leu |
|---|---|---|---|---|---|---|---|---|---|---|---|---|---|---|---|
| | | | 340 | | | | 345 | | | | | 350 | | | |

| Thr | Arg | Glu | Ser | Gly | Tyr | Pro | Gln | Val | Phe | Tyr | Gly | Asp | Met | Tyr | Gly |
|---|---|---|---|---|---|---|---|---|---|---|---|---|---|---|---|
| | | 355 | | | | | 360 | | | | | 365 | | | |

| Thr | Lys | Gly | Asp | Ser | Gln | Arg | Glu | Ile | Pro | Ala | Leu | Lys | His | Lys | Ile |
|---|---|---|---|---|---|---|---|---|---|---|---|---|---|---|---|
| | 370 | | | | | 375 | | | | | 380 | | | | |

| Glu | Pro | Ile | Leu | Lys | Ala | Arg | Lys | Gln | Tyr | Ala | Tyr | Gly | Ala | Gln | His |
|---|---|---|---|---|---|---|---|---|---|---|---|---|---|---|---|
| 385 | | | | | 390 | | | | | 395 | | | | | 400 |

| Asp | Tyr | Phe | Asp | His | His | Asp | Ile | Val | Gly | Trp | Thr | Arg | Glu | Gly | Asp |
|---|---|---|---|---|---|---|---|---|---|---|---|---|---|---|---|
| | | | | 405 | | | | | 410 | | | | | 415 | |

-continued

```
Ser  Ser  Val  Ala  Asn  Ser  Gly  Leu  Ala  Ala  Leu  Ile  Thr  Asp  Gly  Pro
               420                 425                           430

Gly  Gly  Ala  Lys  Arg  Met  Tyr  Val  Gly  Arg  Gln  Asn  Ala  Gly  Glu  Thr
               435                 440                           445

Trp  His  Asp  Ile  Thr  Gly  Asn  Arg  Ser  Glu  Pro  Val  Ile  Asn  Ser
     450                           455                 460

Glu  Gly  Trp  Gly  Glu  Phe  His  Val  Asn  Gly  Gly  Ser  Val  Ser  Ile  Tyr
465                      470                      475                      480

Val  Gln  Arg
```

( 2 ) INFORMATION FOR SEQ ID NO:33:

( i ) SEQUENCE CHARACTERISTICS:
        ( A ) LENGTH: 511 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:33:

```
Met  Lys  Gln  Gln  Lys  Arg  Leu  Tyr  Ala  Arg  Leu  Leu  Thr  Leu  Leu  Phe
1                   5                        10                          15

Ala  Leu  Ile  Phe  Leu  Leu  Pro  His  Ser  Ala  Ala  Ala  Ala  Asn  Leu
               20                  25                            30

Asn  Gly  Thr  Leu  Met  Gln  Tyr  Phe  Glu  Trp  Tyr  Met  Pro  Asn  Asp  Gly
          35                       40                      45

His  Trp  Lys  Arg  Leu  Gln  Asn  Asp  Ser  Ala  Tyr  Leu  Ala  Glu  His  Gly
     50                       55                      60

Ile  Thr  Ala  Val  Trp  Ile  Pro  Pro  Ala  Tyr  Lys  Gly  Thr  Ser  Gln  Ala
65                       70                      75                           80

Asp  Val  Gly  Tyr  Gly  Ala  Tyr  Asp  Leu  Tyr  Asp  Leu  Gly  Glu  Phe  His
               85                       90                      95

Gln  Lys  Gly  Thr  Val  Arg  Thr  Lys  Tyr  Gly  Thr  Lys  Gly  Glu  Leu  Gln
               100                      105                     110

Ser  Ala  Ile  Lys  Ser  Leu  His  Ser  Arg  Asp  Ile  Asn  Val  Tyr  Gly  Asp
               115                      120                     125

Val  Val  Ile  Asn  His  Lys  Gly  Gly  Ala  Asp  Ala  Thr  Glu  Asp  Val  Thr
     130                       135                      140

Ala  Val  Glu  Val  Asp  Pro  Ala  Asp  Arg  Asn  Arg  Val  Ile  Ser  Gly  Glu
145                      150                      155                          160

His  Leu  Ile  Lys  Ala  Trp  Thr  His  Phe  His  Phe  Pro  Gly  Arg  Gly  Ser
               165                      170                      175

Thr  Tyr  Ser  Asp  Phe  Lys  Trp  His  Trp  Tyr  His  Phe  Asp  Gly  Thr  Asp
               180                      185                      190

Trp  Asp  Glu  Ser  Arg  Lys  Leu  Asn  Arg  Ile  Tyr  Lys  Phe  Gln  Gly  Lys
               195                      200                      205

Ala  Trp  Asp  Trp  Glu  Val  Ser  Asn  Glu  Asn  Gly  Asn  Tyr  Asp  Tyr  Leu
               210                      215                      220

Met  Tyr  Ala  Asp  Ile  Asp  Tyr  Asp  His  Pro  Asp  Val  Ala  Ala  Glu  Ile
225                      230                      235                          240

Lys  Arg  Trp  Gly  Thr  Trp  Tyr  Ala  Asn  Glu  Leu  Gln  Leu  Asp  Gly  Phe
                    245                      250                      255

Arg  Leu  Asp  Ala  Val  Lys  His  Ile  Lys  Phe  Ser  Phe  Leu  Arg  Asp  Trp
               260                      265                      270

Val  Asn  His  Val  Arg  Glu  Lys  Thr  Gly  Lys  Glu  Met  Phe  Thr  Val  Ala
               275                      280                      285
```

```
Glu  Tyr  Trp  Gln  Asn  Asp  Leu  Gly  Ala  Leu  Glu  Asn  Tyr  Leu  Asn  Lys
     290                 295                      300

Thr  Asn  Phe  Asn  His  Ser  Val  Phe  Asp  Val  Pro  Leu  His  Tyr  Gln  Phe
305                      310                      315                      320

His  Ala  Ala  Ser  Thr  Gln  Gly  Gly  Gly  Tyr  Asp  Met  Arg  Lys  Leu  Leu
                    325                      330                      335

Asn  Gly  Thr  Val  Val  Ser  Lys  His  Pro  Leu  Lys  Ser  Val  Thr  Phe  Val
               340                      345                      350

Asp  Asn  His  Asp  Thr  Gln  Pro  Gly  Gln  Ser  Leu  Glu  Ser  Thr  Val  Gln
          355                      360                      365

Thr  Trp  Phe  Lys  Pro  Leu  Ala  Tyr  Ala  Phe  Ile  Leu  Thr  Arg  Glu  Ser
     370                      375                      380

Gly  Tyr  Pro  Gln  Val  Phe  Tyr  Gly  Asp  Met  Tyr  Gly  Thr  Lys  Gly  Asp
385                           390                      395                      400

Ser  Gln  Arg  Glu  Ile  Pro  Ala  Leu  Lys  His  Lys  Ile  Glu  Pro  Ile  Leu
                    405                      410                      415

Lys  Ala  Arg  Lys  Gln  Tyr  Ala  Tyr  Gly  Ala  Gln  His  Asp  Tyr  Phe  Asp
               420                      425                      430

His  His  Asp  Ile  Val  Gly  Trp  Thr  Arg  Glu  Gly  Asp  Ser  Val  Ala
          435                      440                      445

Asn  Ser  Gly  Leu  Ala  Ala  Leu  Ile  Thr  Asp  Gly  Pro  Gly  Gly  Ala  Lys
     450                      455                      460

Arg  Met  Tyr  Val  Gly  Arg  Gln  Asn  Ala  Gly  Glu  Thr  Trp  His  Asp  Ile
465                           470                      475                      480

Thr  Gly  Asn  Arg  Ser  Glu  Pro  Val  Val  Ile  Asn  Ser  Glu  Gly  Trp  Gly
                    485                      490                      495

Glu  Phe  His  Val  Asn  Gly  Gly  Ser  Val  Ser  Ile  Tyr  Val  Gln  Arg
               500                      505                      510
```

( 2 ) INFORMATION FOR SEQ ID NO:34:

( i ) SEQUENCE CHARACTERISTICS:
        ( A ) LENGTH: 520 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:34:

```
Met  Arg  Gly  Arg  Gly  Asn  Met  Ile  Gln  Lys  Arg  Lys  Arg  Thr  Val  Ser
1                   5                        10                       15

Phe  Arg  Leu  Val  Leu  Met  Cys  Thr  Leu  Leu  Phe  Val  Ser  Leu  Pro  Ile
               20                       25                       30

Thr  Lys  Thr  Ser  Ala  Val  Asn  Gly  Thr  Leu  Met  Gln  Tyr  Phe  Glu  Trp
               35                       40                       45

Tyr  Thr  Pro  Asn  Asp  Gly  Gln  His  Trp  Lys  Arg  Leu  Gln  Asn  Asp  Ala
     50                       55                       60

Glu  His  Leu  Ser  Asp  Ile  Gly  Ile  Thr  Ala  Val  Trp  Ile  Pro  Pro  Ala
65                            70                       75                       80

Tyr  Lys  Gly  Leu  Ser  Gln  Ser  Asp  Asn  Gly  Tyr  Gly  Pro  Tyr  Asp  Leu
               85                       90                       95

Tyr  Asp  Leu  Gly  Glu  Phe  Gln  Gln  Lys  Gly  Thr  Val  Arg  Thr  Lys  Tyr
               100                      105                      110

Gly  Thr  Lys  Ser  Glu  Leu  Gln  Asp  Ala  Ile  Gly  Ser  Leu  His  Ser  Arg
               115                      120                      125
```

```
Asn Val Gln Val Tyr Gly Asp Val Val Leu Asn His Lys Ala Gly Ala
    130             135             140

Asp Ala Thr Glu Asp Val Thr Ala Val Glu Val Asn Pro Ala Asn Arg
145             150             155             160

Asn Gln Glu Thr Ser Glu Glu Tyr Gln Ile Lys Ala Trp Thr Asp Phe
                165             170             175

Arg Phe Pro Gly Arg Gly Asn Thr Tyr Ser Asp Phe Lys Trp His Trp
            180             185             190

Tyr His Phe Asp Gly Ala Asp Trp Asp Glu Ser Arg Lys Ile Ser Arg
        195             200             205

Ile Phe Lys Phe Arg Gly Glu Gly Lys Ala Trp Asp Trp Glu Val Ser
    210             215             220

Ser Glu Asn Gly Asn Tyr Asp Tyr Leu Met Tyr Ala Asp Val Asp Tyr
225             230             235             240

Asp His Pro Asp Val Val Ala Glu Thr Lys Lys Trp Gly Ile Trp Tyr
                245             250             255

Ala Asn Glu Leu Ser Leu Asp Gly Phe Arg Ile Asp Ala Ala Lys His
            260             265             270

Ile Lys Phe Ser Phe Leu Arg Asp Trp Val Gln Ala Val Arg Gln Ala
    275             280             285

Thr Gly Lys Glu Met Phe Thr Val Ala Glu Tyr Trp Gln Asn Asn Ala
    290             295             300

Gly Lys Leu Glu Asn Tyr Leu Asn Lys Thr Ser Phe Asn Gln Ser Val
305             310             315             320

Phe Asp Val Pro Leu His Phe Asn Leu Gln Ala Ala Ser Ser Gln Gly
                325             330             335

Gly Gly Tyr Asp Met Arg Arg Leu Leu Asp Gly Thr Val Val Ser Arg
            340             345             350

His Pro Glu Lys Ala Val Thr Phe Val Glu Asn His Asp Thr Gln Pro
        355             360             365

Gly Gln Ser Leu Glu Ser Thr Val Gln Thr Trp Phe Lys Pro Leu Ala
    370             375             380

Tyr Ala Phe Ile Leu Thr Arg Glu Ser Gly Tyr Pro Gln Val Phe Tyr
385             390             395             400

Gly Asp Met Tyr Gly Thr Lys Gly Thr Ser Pro Lys Glu Ile Pro Ser
                405             410             415

Leu Lys Asp Asn Ile Glu Pro Ile Leu Lys Ala Arg Lys Glu Tyr Ala
            420             425             430

Tyr Gly Pro Gln His Asp Tyr Ile Asp His Pro Asp Val Ile Gly Trp
        435             440             445

Thr Arg Glu Gly Asp Ser Ser Ala Ala Lys Ser Gly Leu Ala Ala Leu
    450             455             460

Ile Thr Asp Gly Pro Gly Gly Ser Lys Arg Met Tyr Ala Gly Leu Lys
465             470             475             480

Asn Ala Gly Glu Thr Trp Tyr Asp Ile Thr Gly Asn Arg Ser Asp Thr
                485             490             495

Val Lys Ile Gly Ser Asp Gly Trp Gly Glu Phe His Val Asn Asp Gly
            500             505             510

Ser Val Ser Ile Tyr Val Gln Lys
        515             520
```

(2) INFORMATION FOR SEQ ID NO:35:

(i) SEQUENCE CHARACTERISTICS:

(A) LENGTH: 548 amino acids (B) TYPE: amino acid
(C) STRANDEDNESS: single
(D) TOPOLOGY: linear (ii) MOLECULE TYPE: protein (xi) SEQUENCE DESCRIPTION: SEQ ID NO:35:

| Val | Leu | Thr | Phe | His | Arg | Ile | Ile | Arg | Lys | Gly | Trp | Met | Phe | Leu | Leu |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ala | Phe | Leu | Leu | Thr | Ala | Ser | Leu | Phe | Cys | Pro | Thr | Gly | Arg | His | Ala |
|     |     |     | 20  |     |     |     | 25  |     |     |     |     |     | 30  |     |     |
| Lys | Ala | Ala | Ala | Pro | Phe | Asn | Gly | Thr | Met | Met | Gln | Tyr | Phe | Glu | Trp |
|     |     | 35  |     |     |     |     | 40  |     |     |     |     | 45  |     |     |     |
| Tyr | Leu | Pro | Asp | Asp | Gly | Thr | Leu | Trp | Thr | Lys | Val | Ala | Asn | Glu | Ala |
|     | 50  |     |     |     |     | 55  |     |     |     |     | 60  |     |     |     |     |
| Asn | Asn | Leu | Ser | Ser | Leu | Gly | Ile | Thr | Ala | Leu | Ser | Leu | Pro | Pro | Ala |
| 65  |     |     |     |     | 70  |     |     |     |     | 75  |     |     |     |     | 80  |
| Tyr | Lys | Gly | Thr | Ser | Arg | Ser | Asp | Val | Gly | Tyr | Gly | Val | Tyr | Asp | Leu |
|     |     |     |     | 85  |     |     |     |     | 90  |     |     |     |     | 95  |     |
| Tyr | Asp | Leu | Gly | Glu | Phe | Asn | Gln | Lys | Gly | Thr | Val | Arg | Thr | Lys | Tyr |
|     |     |     | 100 |     |     |     |     | 105 |     |     |     |     | 110 |     |     |
| Gly | Thr | Lys | Ala | Gln | Tyr | Leu | Gln | Ala | Ile | Gln | Ala | Ala | His | Ala | Ala |
|     |     | 115 |     |     |     |     | 120 |     |     |     |     | 125 |     |     |     |
| Gly | Met | Gln | Val | Tyr | Ala | Asp | Val | Val | Phe | Asp | His | Lys | Gly | Gly | Ala |
|     | 130 |     |     |     |     | 135 |     |     |     |     | 140 |     |     |     |     |
| Asp | Gly | Thr | Glu | Trp | Val | Asp | Ala | Val | Glu | Val | Asn | Pro | Ser | Asp | Arg |
| 145 |     |     |     |     | 150 |     |     |     |     | 155 |     |     |     |     | 160 |
| Asn | Gln | Glu | Ile | Ser | Gly | Thr | Tyr | Gln | Ile | Gln | Ala | Trp | Thr | Lys | Phe |
|     |     |     |     | 165 |     |     |     |     | 170 |     |     |     |     | 175 |     |
| Asp | Phe | Pro | Gly | Arg | Gly | Asn | Thr | Tyr | Ser | Ser | Phe | Lys | Trp | Arg | Trp |
|     |     |     | 180 |     |     |     |     | 185 |     |     |     |     | 190 |     |     |
| Tyr | His | Phe | Asp | Gly | Val | Asp | Trp | Asp | Glu | Ser | Arg | Lys | Leu | Ser | Arg |
|     |     | 195 |     |     |     |     | 200 |     |     |     |     | 205 |     |     |     |
| Ile | Tyr | Lys | Phe | Arg | Gly | Ile | Gly | Lys | Ala | Trp | Asp | Trp | Glu | Val | Asp |
|     | 210 |     |     |     |     | 215 |     |     |     |     | 220 |     |     |     |     |
| Thr | Glu | Asn | Gly | Asn | Tyr | Asp | Tyr | Leu | Met | Tyr | Ala | Asp | Leu | Asp | Met |
| 225 |     |     |     |     | 230 |     |     |     |     | 235 |     |     |     |     | 240 |
| Asp | His | Pro | Glu | Val | Val | Thr | Glu | Leu | Lys | Asn | Trp | Gly | Lys | Trp | Tyr |
|     |     |     |     | 245 |     |     |     |     | 250 |     |     |     |     | 255 |     |
| Val | Asn | Thr | Thr | Asn | Ile | Asp | Gly | Phe | Arg | Leu | Asp | Gly | Leu | Lys | His |
|     |     |     | 260 |     |     |     |     | 265 |     |     |     |     | 270 |     |     |
| Ile | Lys | Phe | Ser | Phe | Phe | Pro | Asp | Trp | Leu | Ser | Tyr | Val | Arg | Ser | Gln |
|     |     | 275 |     |     |     |     | 280 |     |     |     |     | 285 |     |     |     |
| Thr | Gly | Lys | Pro | Leu | Phe | Thr | Val | Gly | Glu | Tyr | Trp | Ser | Tyr | Asp | Ile |
|     | 290 |     |     |     |     | 295 |     |     |     |     | 300 |     |     |     |     |
| Asn | Lys | Leu | His | Asn | Tyr | Ile | Thr | Lys | Thr | Asn | Gly | Thr | Met | Ser | Leu |
| 305 |     |     |     |     | 310 |     |     |     |     | 315 |     |     |     |     | 320 |
| Phe | Asp | Ala | Pro | Leu | His | Asn | Lys | Phe | Tyr | Thr | Ala | Ser | Lys | Ser | Gly |
|     |     |     |     | 325 |     |     |     |     | 330 |     |     |     |     | 335 |     |
| Gly | Ala | Phe | Asp | Met | Arg | Thr | Leu | Met | Thr | Asn | Thr | Leu | Met | Lys | Asp |
|     |     |     | 340 |     |     |     |     | 345 |     |     |     |     | 350 |     |     |
| Gln | Pro | Thr | Leu | Ala | Val | Thr | Phe | Val | Asp | Asn | His | Asp | Thr | Asn | Pro |
|     |     | 355 |     |     |     |     | 360 |     |     |     |     | 365 |     |     |     |
| Ala | Lys | Arg | Cys | Ser | His | Gly | Arg | Pro | Trp | Phe | Lys | Pro | Leu | Ala | Tyr |
|     | 370 |     |     |     |     | 375 |     |     |     |     | 380 |     |     |     |     |

```
Ala  Phe  Ile  Leu  Thr  Arg  Gln  Glu  Gly  Tyr  Pro  Cys  Val  Phe  Tyr  Gly
385                 390                 395                           400

Asp  Tyr  Tyr  Gly  Ile  Pro  Gln  Tyr  Asn  Ile  Pro  Ser  Leu  Lys  Ser  Lys
                    405                 410                      415

Ile  Asp  Pro  Leu  Leu  Ile  Ala  Arg  Arg  Asp  Tyr  Ala  Tyr  Gly  Thr  Gln
               420                 425                      430

His  Asp  Tyr  Leu  Asp  His  Ser  Asp  Ile  Ile  Gly  Trp  Thr  Arg  Glu  Gly
          435                      440                      445

Val  Thr  Glu  Lys  Pro  Gly  Ser  Gly  Leu  Ala  Ala  Leu  Ile  Thr  Asp  Gly
     450                      455                      460

Ala  Gly  Arg  Ser  Lys  Trp  Met  Tyr  Val  Gly  Lys  Gln  His  Ala  Gly  Lys
465                      470                      475                      480

Val  Phe  Tyr  Asp  Leu  Thr  Gly  Asn  Arg  Ser  Asp  Thr  Val  Thr  Ile  Asn
               485                      490                      495

Ser  Asp  Gly  Trp  Gly  Glu  Phe  Lys  Val  Asn  Gly  Gly  Ser  Val  Ser  Val
               500                      505                 510

Trp  Val  Pro  Arg  Lys  Thr  Thr  Val  Ser  Thr  Ile  Ala  Arg  Pro  Ile  Thr
          515                      520                 525

Thr  Arg  Pro  Trp  Thr  Gly  Glu  Phe  Val  Arg  Trp  His  Glu  Pro  Arg  Leu
     530                      535                 540

Val  Ala  Trp  Pro
545
```

(2) INFORMATION FOR SEQ ID NO:36:

(i) SEQUENCE CHARACTERISTICS:
        (A) LENGTH: 483 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:36:

```
Ala  Asn  Leu  Asn  Gly  Thr  Leu  Met  Gln  Tyr  Phe  Glu  Trp  Tyr  Met  Pro
1                   5                   10                       15

Asn  Asp  Gly  Gln  His  Trp  Lys  Arg  Leu  Gln  Asn  Asp  Ser  Ala  Tyr  Leu
               20                 25                      30

Ala  Glu  His  Gly  Ile  Thr  Ala  Val  Trp  Ile  Pro  Pro  Ala  Tyr  Lys  Gly
          35                      40                      45

Thr  Ser  Gln  Ala  Asp  Val  Gly  Tyr  Gly  Ala  Tyr  Asp  Leu  Tyr  Asp  Leu
     50                      55                      60

Gly  Glu  Phe  His  Gln  Lys  Gly  Thr  Val  Arg  Thr  Lys  Tyr  Gly  Thr  Lys
65                      70                      75                      80

Gly  Glu  Leu  Gln  Ser  Ala  Ile  Lys  Ser  Leu  His  Ser  Arg  Asp  Ile  Asn
               85                      90                      95

Val  Tyr  Gly  Asp  Val  Val  Ile  Asn  His  Lys  Gly  Gly  Ala  Asp  Ala  Thr
               100                     105                     110

Glu  Asp  Val  Thr  Ala  Val  Glu  Val  Asp  Pro  Ala  Asp  Arg  Asn  Arg  Val
          115                     120                     125

Ile  Ser  Gly  Glu  His  Leu  Ile  Lys  Ala  Trp  Thr  His  Phe  His  Phe  Pro
     130                     135                     140

Gly  Arg  Gly  Ser  Thr  Tyr  Ser  Asp  Phe  Lys  Trp  His  Trp  Tyr  His  Phe
145                     150                     155                     160

Asp  Gly  Thr  Asp  Trp  Asp  Glu  Ser  Arg  Lys  Leu  Asn  Arg  Ile  Tyr  Lys
               165                     170                     175

Phe  Gln  Gly  Lys  Ala  Trp  Asp  Trp  Glu  Val  Ser  Asn  Glu  Asn  Gly  Asn
```

|     |     |     |     |     | 180 |     |     |     |     | 185 |     |     |     |     | 190 |     |
| --- | --- | --- | --- | --- | --- | --- | --- | --- | --- | --- | --- | --- | --- | --- | --- | --- |
| Tyr | Asp | Tyr 195 | Leu | Thr | Tyr | Ala | Asp 200 | Ile | Asp | Tyr | Asp 205 | His | Pro | Asp | Val |
| Ala | Ala 210 | Glu | Ile | Lys | Arg | Trp 215 | Gly | Thr | Trp | Tyr | Ala 220 | Asn | Glu | Leu | Gln |
| Leu 225 | Asp | Gly | Phe | Arg | Leu 230 | Asp | Ala | Val | Lys | His 235 | Ile | Lys | Phe | Ser | Phe 240 |
| Leu | Arg | Asp | Trp | Val 245 | Asn | His | Val | Arg | Glu 250 | Lys | Thr | Gly | Lys | Glu 255 | Met |
| Phe | Thr | Val | Ala 260 | Glu | Tyr | Trp | Gln | Asn 265 | Asp | Leu | Gly | Ala | Leu 270 | Glu | Asn |
| Tyr | Leu | Asn 275 | Lys | Thr | Asn | Phe | Asn 280 | His | Ser | Val | Phe | Asp 285 | Val | Pro | Leu |
| His | Tyr 290 | Gln | Phe | His | Ala | Ala 295 | Ser | Thr | Gln | Gly | Gly 300 | Gly | Tyr | Asp | Met |
| Arg 305 | Lys | Leu | Leu | Asn | Gly 310 | Thr | Val | Val | Ser | Lys 315 | His | Pro | Leu | Lys | Ser 320 |
| Val | Thr | Phe | Val | Asp 325 | Asn | His | Asp | Thr | Gln 330 | Pro | Gly | Gln | Ser | Leu 335 | Glu |
| Ser | Thr | Val | Gln 340 | Thr | Trp | Phe | Lys | Pro 345 | Leu | Ala | Tyr | Ala | Phe 350 | Ile | Leu |
| Thr | Arg | Glu 355 | Ser | Gly | Tyr | Pro | Gln 360 | Val | Phe | Tyr | Gly | Asp 365 | Met | Tyr | Gly |
| Thr | Lys 370 | Gly | Asp | Ser | Gln | Arg 375 | Glu | Ile | Pro | Ala | Leu 380 | Lys | His | Lys | Ile |
| Glu 385 | Pro | Ile | Leu | Lys | Ala 390 | Arg | Lys | Gln | Tyr | Ala 395 | Tyr | Gly | Ala | Gln | His 400 |
| Asp | Tyr | Phe | Asp | His 405 | His | Asp | Ile | Val | Gly 410 | Trp | Thr | Arg | Glu | Gly 415 | Asp |
| Ser | Ser | Val | Ala 420 | Asn | Ser | Gly | Leu 425 | Ala | Ala | Leu | Ile | Thr 430 | Asp | Gly | Pro |
| Gly | Gly | Ala 435 | Lys | Arg | Met | Tyr | Val 440 | Gly | Arg | Gln | Asn | Ala 445 | Gly | Glu | Thr |
| Trp | His 450 | Asp | Ile | Thr | Gly | Asn 455 | Arg | Ser | Glu | Pro | Val 460 | Val | Ile | Asn | Ser |
| Glu 465 | Gly | Trp | Gly | Glu | Phe 470 | His | Val | Asn | Gly | Gly 475 | Ser | Val | Ser | Ile | Tyr 480 |
| Val | Gln | Arg |     |     |     |     |     |     |     |     |     |     |     |     |     |

( 2 ) INFORMATION FOR SEQ ID NO:37:

( i ) SEQUENCE CHARACTERISTICS:
        ( A ) LENGTH: 487 amino acids
        ( B ) TYPE: amino acid
        ( C ) STRANDEDNESS: single
        ( D ) TOPOLOGY: linear ( i i ) MOLECULE TYPE: protein ( x i ) SEQUENCE DESCRIPTION: SEQ ID NO:37:

| Ala 1 | Ala | Ala | Ala | Ala 5 | Asn | Leu | Asn | Gly | Thr 10 | Leu | Met | Gln | Tyr | Phe 15 | Glu |
| --- | --- | --- | --- | --- | --- | --- | --- | --- | --- | --- | --- | --- | --- | --- | --- |
| Trp | Tyr | Met | Pro 20 | Asn | Asp | Gly | Gln | His 25 | Trp | Lys | Arg | Leu | Gln 30 | Asn | Asp |
| Ser | Ala | Tyr 35 | Leu | Ala | Glu | His | Gly 40 | Ile | Thr | Ala | Val | Trp 45 | Ile | Pro | Pro |

```
Ala  Tyr  Lys  Gly  Thr  Ser  Gln  Ala  Asp  Val  Gly  Tyr  Gly  Ala  Tyr  Asp
     50                  55                  60

Leu  Tyr  Asp  Leu  Gly  Glu  Phe  His  Gln  Lys  Gly  Thr  Val  Arg  Thr  Lys
65                       70                  75                            80

Tyr  Gly  Thr  Lys  Gly  Glu  Leu  Gln  Ser  Ala  Ile  Lys  Ser  Leu  His  Ser
                    85                       90                       95

Arg  Asp  Ile  Asn  Val  Tyr  Gly  Asp  Val  Val  Ile  Asn  His  Lys  Gly  Gly
               100                 105                      110

Ala  Asp  Ala  Thr  Glu  Asp  Val  Thr  Ala  Val  Glu  Val  Asp  Pro  Ala  Asp
               115                 120                      125

Arg  Asn  Arg  Val  Ile  Ser  Gly  Glu  His  Leu  Ile  Lys  Ala  Trp  Thr  His
     130                      135                      140

Phe  His  Phe  Pro  Gly  Arg  Gly  Ser  Thr  Tyr  Ser  Asp  Phe  Lys  Trp  His
145                      150                 155                           160

Trp  Tyr  His  Phe  Asp  Gly  Thr  Asp  Trp  Asp  Glu  Ser  Arg  Lys  Leu  Asn
               165                      170                      175

Arg  Ile  Tyr  Lys  Phe  Gln  Gly  Lys  Ala  Trp  Asp  Trp  Glu  Val  Ser  Asn
               180                 185                      190

Glu  Asn  Gly  Asn  Tyr  Asp  Tyr  Leu  Met  Tyr  Ala  Asp  Ile  Asp  Tyr  Asp
          195                      200                 205

His  Pro  Asp  Val  Ala  Ala  Glu  Ile  Lys  Arg  Trp  Gly  Thr  Trp  Tyr  Ala
     210                      215                      220

Asn  Glu  Leu  Gln  Leu  Asp  Gly  Phe  Arg  Leu  Asp  Ala  Val  Lys  His  Ile
225                      230                 235                           240

Lys  Phe  Ser  Phe  Leu  Arg  Asp  Trp  Val  Asn  His  Val  Arg  Glu  Lys  Thr
                    245                      250                      255

Gly  Lys  Glu  Met  Phe  Thr  Val  Ala  Glu  Tyr  Trp  Gln  Asn  Asp  Leu  Gly
               260                 265                      270

Ala  Leu  Glu  Asn  Tyr  Leu  Asn  Lys  Thr  Asn  Phe  Asn  His  Ser  Val  Phe
          275                      280                 285

Asp  Val  Pro  Leu  His  Tyr  Gln  Phe  His  Ala  Ala  Ser  Thr  Gln  Gly  Gly
          290                      295                 300

Gly  Tyr  Asp  Met  Arg  Lys  Leu  Leu  Asn  Gly  Thr  Val  Val  Ser  Lys  His
305                      310                 315                           320

Pro  Leu  Lys  Ser  Val  Thr  Phe  Val  Asp  Asn  His  Asp  Thr  Gln  Pro  Gly
                    325                      330                      335

Gln  Ser  Leu  Glu  Ser  Thr  Val  Gln  Thr  Trp  Phe  Lys  Pro  Leu  Ala  Tyr
               340                 345                      350

Ala  Phe  Ile  Leu  Thr  Arg  Glu  Ser  Gly  Tyr  Pro  Gln  Val  Phe  Tyr  Gly
          355                      360                 365

Asp  Met  Tyr  Gly  Thr  Lys  Gly  Asp  Ser  Gln  Arg  Glu  Ile  Pro  Ala  Leu
     370                      375                      380

Lys  His  Lys  Ile  Glu  Pro  Ile  Leu  Lys  Ala  Arg  Lys  Gln  Tyr  Ala  Tyr
385                      390                 395                           400

Gly  Ala  Gln  His  Asp  Tyr  Phe  Asp  His  His  Asp  Ile  Val  Gly  Trp  Thr
               405                 410                      415

Arg  Glu  Gly  Asp  Ser  Ser  Val  Ala  Asn  Ser  Gly  Leu  Ala  Ala  Leu  Ile
               420                      425                      430

Thr  Asp  Gly  Pro  Gly  Gly  Ala  Lys  Arg  Met  Tyr  Val  Gly  Arg  Gln  Asn
          435                      440                      445

Ala  Gly  Glu  Thr  Trp  His  Asp  Ile  Thr  Gly  Asn  Arg  Ser  Glu  Pro  Val
     450                      455                      460

Val  Ile  Asn  Ser  Glu  Gly  Trp  Gly  Glu  Phe  His  Val  Asn  Gly  Gly  Ser
465                      470                      475                      480
```

Val Ser Ile Tyr Val Gln Arg
                485

(2) INFORMATION FOR SEQ ID NO:38:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:38:

Met Lys Gln Gln Lys Arg Leu Thr Ala Arg Leu Leu Thr Leu Leu Phe
1               5                   10                  15

Ala Leu Ile Phe Leu Leu Pro His Ser Ala Ala Ala Ala Ala Asn Leu
            20                  25                  30

(2) INFORMATION FOR SEQ ID NO:39:

(i) SEQUENCE CHARACTERISTICS:
        (A) LENGTH: 33 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:39:

Met Arg Ser Lys Thr Leu Trp Ile Ser Leu Leu Phe Ala Leu Thr Leu
1               5                   10                  15

Ile Phe Thr Met Ala Phe Ser Asn Met Ser Ala Gln Ala Ala Gly Lys
            20                  25                  30

Ser (2) INFORMATION FOR SEQ ID NO:40:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:40:

Met Arg Ser Lys Thr Leu Trp Ile Ser Leu Leu Phe Ala Leu Thr Leu
1               5                   10                  15

Ile Phe Thr Met Ala Phe Ser Asn Met Ser Ala Gln Ala Ala Ala Ala
            20                  25                  30

Ala Ala Asn
        35

(2) INFORMATION FOR SEQ ID NO:41:

(i) SEQUENCE CHARACTERISTICS:
        (A) LENGTH: 32 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:41:

Met Arg Ser Lys Thr Leu Trp Ile Ser Leu Leu Phe Ala Leu Thr Leu

```
             1               5                    10                   15
        Ile Phe Thr Met Ala Phe Ser Asn Met Ser Ala Gln Ala Ala Asn Leu
                     20                  25                  30
```

( 2 ) INFORMATION FOR SEQ ID NO:42:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:42:

```
CACCTAATTA AAGCTTTCAC ACATTTTCAT TTT                                    33
```

( 2 ) INFORMATION FOR SEQ ID NO:43:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:43:

```
CACCTAATTA AAGCTTACAC ACATTTTCAT TTT                                    33
```

( 2 ) INFORMATION FOR SEQ ID NO:44:

( i ) SEQUENCE CHARACTERISTICS:
        ( A ) LENGTH: 66 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:44:

```
CCGCGTAATT TCCGGAGAAC ACCTAATTAA AGCCGCAACA CATTTTCATT TTCCCGGGCG       60
CGGCAG                                                                  66
```

( 2 ) INFORMATION FOR SEQ ID NO:45:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:45:

```
CCGGAGAACA CCTAATTAAA GCCCTAACAC ATTTTCATTT TC                          42
```

( 2 ) INFORMATION FOR SEQ ID NO:46:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:46:

CCGGAGAACA CCTAATTAAA GCCCACACAC ATTTTCATTT TC        42

(2) INFORMATION FOR SEQ ID NO:47:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:47:

CCGGAGAACA CCTAATTAAA GCCTGCACAC ATTTTCATTT TC        42

(2) INFORMATION FOR SEQ ID NO:48:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:48:

GATGCAGTAT TTCGAACTGG TATA        24

(2) INFORMATION FOR SEQ ID NO:49:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:49:

TGCCCAATGA TGGCCAACAT TGGAAG        26

(2) INFORMATION FOR SEQ ID NO:50:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:50:

CGAATGGTAT GCTCCCAATG ACGG        24

(2) INFORMATION FOR SEQ ID NO:51:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:51:

CGAATGGTAT CGCCCCAATG ACGG        24

(2) INFORMATION FOR SEQ ID NO:52:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:52:

CGAATGGTAT AATCCCAATG ACGG 24

( 2 ) INFORMATION FOR SEQ ID NO:53:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:53:

CGAATGGTAT GATCCCAATG ACGG 24

( 2 ) INFORMATION FOR SEQ ID NO:54:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:54:

CGAATGGTAT CACCCCAATG ACGG 24

( 2 ) INFORMATION FOR SEQ ID NO:55:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:55:

CGAATGGTAT AAACCCAATG ACGG 24

( 2 ) INFORMATION FOR SEQ ID NO:56:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:56:

CGAATGGTAT CCGCCCAATG ACGG 24

( 2 ) INFORMATION FOR SEQ ID NO:57:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:57:

CGAATGGTAT TCTCCCAATG ACGG 24

( 2 ) INFORMATION FOR SEQ ID NO:58:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:58:

CGAATGGTAC ACTCCCAATG ACGG 24

( 2 ) INFORMATION FOR SEQ ID NO:59:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:59:

CGAATGGTAT GTTCCCAATG ACGG 24

( 2 ) INFORMATION FOR SEQ ID NO:60:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:60:

CGAATGGTAT TGTCCCAATG ACGG 24

( 2 ) INFORMATION FOR SEQ ID NO:61:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:61:

CGAATGGTAT CAACCCAATG ACGG 24

( 2 ) INFORMATION FOR SEQ ID NO:62:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:62:

CGAATGGTAT GAACCCAATG ACGG                    24

( 2 ) INFORMATION FOR SEQ ID NO:63:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:63:

CGAATGGTAT GGTCCCAATG ACGG                    24

( 2 ) INFORMATION FOR SEQ ID NO:64:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:64:

CGAATGGTAT ATTCCCAATG ACGG                    24

( 2 ) INFORMATION FOR SEQ ID NO:65:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:65:

CGAATGGTAT TTTCCCAATG ACGG                    24

( 2 ) INFORMATION FOR SEQ ID NO:66:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:66:

CGAATGGTAC TGGCCCAATG ACGG                    24

( 2 ) INFORMATION FOR SEQ ID NO:67:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:67:

CGAATGGTAT TATCCCAATG ACGG                    24

( 2 ) INFORMATION FOR SEQ ID NO:68:

( i ) SEQUENCE CHARACTERISTICS:
    ( A ) LENGTH: 24 base pairs
    ( B ) TYPE: nucleic acid
    ( C ) STRANDEDNESS: single
    ( D ) TOPOLOGY: linear ( i i ) MOLECULE TYPE: DNA (genomic)

( x i ) SEQUENCE DESCRIPTION: SEQ ID NO:68:

CCGTCATTGG GACTACGTAC CATT     2 4

OXIDATIVLEY STABLE ALPHA-AMYLASE

RELATED APPLICATIONS

This is a divisional of U.S. Ser. No. 08/194,664 filed Feb. 10, 1994, now pending which is a continuation-in-part of U.S. Ser. No. 08/016,395 filed Feb. 11, 1993 now abandoned.

FIELD OF INVENTION

The present invention relates to novel alpha-amylase mutants having an amino acid sequence not found in nature, such mutants having an amino acid sequence wherein one or more amino acid residue(s) of a precursor alpha-amylase, specifically any oxidizable amino acid, have been substituted with a different amino acid. The mutant enzymes of the present invention exhibit altered stability/activity profiles including but not limited to altered oxidative stability, altered pH performance profile, altered specific activity and/or altered thermostability.

BACKGROUND OF THE INVENTION

Alpha-amylases (alpha-1,4-glucan-4-glucanohydrolase, EC3.2.1.1) hydrolyze internal alpha-1,4-glucosidic linkages in starch largely at random, to produce smaller molecular weight malto-dextrins. Alpha-amylases are of considerable commercial value, being used in the initial stages (liquefaction) of starch processing; in alcohol production; as cleaning agents in detergent matrices; and in the textile industry for starch desizing. Alpha-amylases are produced by a wide variety of microorganisms including Bacillus and Aspergillus, with most commercial amylases being produced from bacterial sources such as B. licheniformis, B. amyloliquefaciens, B. subtilis, or B. stearothermophilus. In recent years the preferred enzymes in commercial use have been those from B. licheniformis because of their heat stability and performance, at least at neutral and mildly alkaline pH's.

Previously there have been studies using recombinant DNA techniques to explore which residues are important for the catalytic activity of amylases and/or to explore the effect of modifying certain amino acids within the active site of various analyses (Vihinen, M. et al. (1990) J. Bichem. 107:267–272; Holm, L. et al. (1990) Protein Engineering 3:181–191; Takase, K. et al. (1992) Biochemica et Biophysica Acta, 1120:281–288; Matsui, I. et al. (1992) Febs Letters Vol. 310, No. 3, pp. 216–218); which residues are important for thermal stability (Suzuki, Y. et al. (1989) J. Biol. Chem. 264:18933–18938); and one group has used such methods to introduce mutations at various histidine residues in a B. licheniformis amylase, the rationale for making substitutions at histidine residues was that B. licheniformis amylase (known to be thermostable) when compared to other similar Bacillus amylases, has an excess of histidines and, therefore, it was suggested that replacing a histidine could affect the thermostability of the enzyme (Declerck, N. et al. (1990) J. Biol. Chem. 265:15481–15488; FR 2 665 178-A1; Joyet, P. et al. (1992) Bio/Technology 10:1579–1583).

It has been found that alpha-amylase is inactivated by hydrogen peroxide and other oxidants at pH's between 4 and 10.5 as described in the examples herein. Commercially, alpha-amylase enzymes can be used under dramatically different conditions such as both high and low pH conditions, depending on the commercial application. For example, alpha-amylases may be used in the liquefaction of starch, a process preferably performed at a low pH (pH<5.5). On the other hand, amylases may be used in commercial dish care or laundry detergents, which often contain oxidants such as bleach or peracids, and which are used in much more alkaline conditions.

In order to alter the stability or activity profile of amylase enzymes under varying conditions, it has been found that selective replacement, substitution or deletion of oxidizable amino acids, such as a methionine, tryptophan, tyrosine, histidine or cysteine, results in an altered profile of the variant enzyme as compared to its precursor. Because currently commercially available amylases are not acceptable (stable) under various conditions, there is a need for an amylase having an altered stability and/or activity profile. This altered stability (oxidative, thermal or pH performance profile) can be achieved while maintaining adequate enzymatic activity, as compared to the wild-type or precursor enzyme. The characteristic affected by introducing such mutations may be a change in oxidative stability while maintaining thermal stability or vice versa. Additionally, the substitution of different amino acids for an oxidizable amino acids in the alpha-amylase precursor sequence or the deletion of one or more oxidizable amino acid(s) may result in altered enzymatic activity at a pH other than that which is considered optimal for the precursor alpha-amylase. In other words, the mutant enzymes of the present invention may also have altered pH performance profiles, which may be due to the enhanced oxidative stability of the enzyme.

SUMMARY OF THE INVENTION

The present invention relates to novel alpha-amylase mutants that are the expression product of a mutated DNA sequence encoding an alpha-amylase, the mutated DNA sequence being derived from a precursor alpha-amylase by the deletion or substitution (replacement) of one or more oxidizable amino acid. In one preferred embodiment of the present invention the mutant result from substituting a different amino acid for one or more methionine residue(s) in the precursor alpha-amylase. In another embodiment of the present invention the mutants comprise a substitution of one or more tryptophan residue alone or in combination with the substitution of one or more methionine residue in the precursor alpha-amylase. Such mutant alpha-amylases, in general, are obtained by in vitro modification of a precursor DNA sequence encoding a naturally occurring or recombinant alpha-amylase to encode the substitution or deletion of one or more amino acid residues in a precursor amino acid sequence.

Preferably the substitution or deletion of one or more amino acids in the amino acid sequence is due to the replacement or deletion of one or more methionine, tryptophan, cysteine, histidine or tyrosine residues in such sequence, most preferably the residue which is changed is a methionine residue. The oxidizable amino acid residues may be replaced by any of the other 20 naturally occurring amino acids. If the desired effect is to alter the oxidative stability of the precursor, the amino acid residue may be substituted with a non-oxidizable amino acid (such as alanine, arginine, asparagine, aspartic acid, glutamic acid, glutamine, glycine, isoleucine, leucine, lysine, phenylalanine, proline, serine, threonine, or valine) or another oxidizable amino acid (such as cysteine, methionine, tryptophan, tyrosine or histidine, listed in order of most easily oxidizable to less readily oxidizable). Likewise, if the desired effect is to alter thermostability, any of the other 20 naturally occurring amino acids may be substituted (i.e., cysteine may be substituted for methionine).

Preferred mutants comprise the substitution of a methionine residue equivalent to any of the methionine residues found in B. licheniformis alpha-amylase (+8, +15, +197, +256, +304, +366 and +438). Most preferably the methionine to be replaced is a methionine at a position equivalent to position +197 or +15 in B. licheniformis alpha-amylase. Preferred substitute amino acids to replace the methionine at position +197 are alanine (A), isoleucine (I), threonine (T) or cysteine (C). The preferred substitute amino acids at position +15 are leucine (L), threonine(T), asparagine (N), aspartate (D), serine (S), valine (V) and isoleucine (I), although other substitute amino acids not specified above may be useful. Two specifically preferred mutants of the present invention are M197T and M15L.

Another embodiment of this invention relates to mutants comprising the substitution of a tryptophan residue equivalent to any of the tryptophan residues found in B. licheniformis alpha-amylase (see FIG. 2). Preferably the tryptophan to be replaced is at a position equivalent to +138 in B. licheniformis alpha-amylase. A mutation (substitution) at a tryptophan residue may be made alone or in combination with mutations at other oxidizable amino acid residues. Specifically, it may be advantageous to modify by substitution at least one tryptophan in combination with at least one methionine (for example, the double mutant +138/+197).

The alpha-amylase mutants of the present invention, in general, exhibit altered oxidative stability in the presence of hydrogen peroxide and other oxidants such as bleach or peracids, or, more specific, milder oxidants such as chloramine-T. Mutant enzymes having enhanced oxidative stability will be useful in extending the shelf life and bleach, perborate, percarbonate or peracid compatibility of amylases used in cleaning products. Similarly, reduced oxidative stability may be useful in industrial processes that require the rapid and efficient quenching of enzymatic activity. The mutant enzymes of the present invention may also demonstrate a broadened pH performance profile whereby mutants such as M15L show stability for low pH starch liquefaction and mutants such as M197T show stability at high pH cleaning product conditions. The mutants of the present invention may also have altered thermal stability whereby the mutant may have enhanced stability at either high or low temperatures. It is understood that any change (increase or decrease) in the mutant's enzymatic characteristic(s), as compared to its precursor, may be beneficial depending on the desired end use of the mutant alpha-amylase.

In addition to starch processing and cleaning applications, variant amylases of the present invention may be used in any application in which known amylases are used, for example, variant amylases can be used in textile processing, food processing, etc. Specifically, it is contemplated that a variant enzyme such as M197C, which is easily inactivated by oxidation, would be useful in a process where it is desirable to completely remove amylase activity at the end of the process, for example, in frozen food processing applications.

The preferred alpha-amylase mutants of the present invention are derived from a Bacillus strain such as B. licheniformis, B. amyloliquefaciens, and B. stearothennophilus, and most preferably from Bacillus licheniformis.

In another aspect of the present invention there is provided a novel form of the alpha-amylase normally produced by B. licheniformis. This novel form, designated as the A4 form, has an additional four alanine residues at the N-terminus of the secreted amylase. (FIG. 4b.) Derivatives or mutants of the A4 form of alpha-amylase are encompassed within the present invention. By derivatives or mutants of the A4 form, it is meant that the present invention comprises the A4 form alpha-amylase containing one or more additional mutations such as, for example, mutation (substitution, replacement or deletion) of one or more oxidizable amino acid(s).

In a composition embodiment of the present invention there are provided detergent compositions, liquid, gel or granular, comprising the alpha-amylase mutants described herein. Particularly preferred are detergent compositions comprising a +197 position mutant either alone or in combination with other enzymes such as endoglycosidases, celluloses, proteases, lipases or other amylase enzymes. Additionally, it is contemplated that the compositions of the present invention may include an alpha-amylase mutant having more than one site-specific mutation.

In yet another composition embodiment of the present invention there are provided compositions useful in starch processing and particularly starch liquefaction. The starch liquefaction compositions of the present invention preferably comprise an alpha-amylase mutant having a substitution or deletion at position M15. Additionally, it is contemplated that such compositions may comprise additional components as known to those skilled in the art, including, for example, antioxidants, calcium, ions, etc.

In a process aspect of the present invention there are provided methods for liquefying starch, and particularly granular starch slurries, from either a wet or dry milled process. Generally, in the first step of the starch degradation process, the starch slurry is gelatinized by heating at a relatively high temperature (up to about 110° C.). After the starch slurry is gelatinized it is liquefied and dextrinized using an alpha-amylase. The conditions for such liquefaction are described in commonly assigned U.S. patent application Ser. Nos. 07/785,624 and 07/785,623 and U.S. Pat. No. 5,180,669, the disclosure of which are incorporated herein by reference. The present method for liquefying starch comprises adding to a starch slurry an effective amount of an alpha-amylase of the present invention, alone or in combination with additional excipients such as an antioxidant, and reacting the slurry for an appropriate time and temperature to liquefy the starch.

A further aspect of the present invention comprises the DNA encoding the mutant alpha-amylases of the present invention (including A4 form and mutants thereof) and expression vectors encoding the DNA as well as host cells transformed with such expression vectors.

BRIEF DESCRIPTION OF THE DRAWINGS

FIG. 1 shows the DNA sequence of the gene for alpha-amylase from B. lichenformis (NCIB8061), Seq ID No 31, and deduced translation product as described in Gray, G. et al. (1986) J. Bacter. 166:635–643.

FIG. 2 shows the amino acid sequence of the mature alpha-amylases enzyme from B. licheniformis (NCIB8061), Seq ID No 32.

FIG. 3 shows an alignment of primary structures of Bacillus alpha-amylases. The B. licheniformis amylase (Am-Lich), Seq ID No 33, is described by Gray, G. et al. (1986) J. Bact. 166:635–643; the B. amyloliquefaciens amylase (Am-Amylo), Seq ID No 34, is described by Takkinen, K. et al. (1983) J. Biol. Chem. 258:1007–1013; and the B. stearothermophilus (Am-Stearo), Seq ID No 35, is described by Ihara, H. et al. (1985) J. Biochem. 98:95103.

FIG. 4a shows the amino acid sequence of the mature alpha-amylase variant M197T, Seq ID No 36.

FIG. 4b shows the amino acid sequence of the A4 form of alpha-amylase from B. licheniformis NCIB8061, Seq ID No 37. Numbering is from the N-terminus, starting with the four additional alanines.

FIG. 5 shows plasmid pA4BL wherein BLAA refers to B. licheniformis alpha-amylase gene, PstI to SstI; Amp$^R$ refers to the ampicillin-resistant gene from pBR322; and CAT refers to the Chloramphenicol-resistant gene from pC194.

FIG. 6 shows the signal sequence-mature protein junctions for B. licheniformis (Seq ID No 38), B. subtilis (Seq ID No 39), B. licheniformis in pA4BL (Seq ID No 40) and B. licheniformis in pBLapr (Seq ID No 41).

FIG. 7a shows inactivation of certain alpha-amylases (Spezyme® AA20 and M197L (A4 form)) with 0.88M $H_2O_2$ at pH 5.0, 25° C.

FIG. 7b shows inactivation of certain alpha-amylases (Spezyme® AA20, M197T) with 0.88M $H_2O_2$ at pH 10.0, 25° C.

FIG. 7c shows inactivation of certain alpha-amylases (Spezyme® AA20, MI5L) with 0.88M $H_2O_2$ at pH 5.0, 25° C.

FIG. 8 shows a schematic for the production of M197X cassette mutants.

FIG. 9 shows expression of M197X variants.

FIG. 10 shows thermal stability of M197X variants at pH 5.0, 5mM $CaCl_2$ at 95° C. for 5 mins.

FIGS. 11a and 11b show inactivation of certain amylases in automatic dish care detergents.

FIG. 11a shows the stability of certain amylases in Cascades ™(a commercially available dish care product) at 65° C. in the presence or absence of starch. FIG. 11b shows the stability of certain amylases in Sunlight™(a commercially available dish care product) at 65° C. in the presence or absence of starch.

FIG. 12 shows a schematic for the production of M15X cassette mutants.

FIG. 13 shows expression of M15X variants.

FIG. 14 shows specific activity of M15X variants on soluble starch.

FIG. 15 shows heat stability of M15X variants at 90° C., pH 5.0, 5 mM $CaCl_2$ 5 mins.

FIG. 16 shows specific activity on starch and soluble substrate, and performance in jet liquefaction at pH 5.5, of M15 variants as a function of percent activity of B. licheniformis wild-type.

FIG. 17 shows the inactivation of B. icheniformis alpha-amylase (AA20 at 0.65 mg/ml) with chloramine-T at pH 8.0 as compared to variants M197A (1.7 mg/ml) and M197L (1.7 mg/ml).

FIG. 18 shows the inactivation of B. licheniformis alpha-amylase (AA20 at 0.22 mg/ml) with chloramine-T at pH 4.0 as compared to variants M197A (4.3 mg/ml) and M197L (0.53 mg/ml).

FIG. 19 shows the reaction of B. licheniformis alpha-amylase (AA20 at 0.75 mg/ml) with chloramine-T at pH 5.0 as compared to double variants M197T/W138F (0.64 mg/ml) and M197T/W138Y (0.60 mg/ml).

DETAILED DESCRIPTION OF THE INVENTION

It is believed that amylases used in starch liquefaction may be subject to some form of inactivation due to some activity present in the starch slurry (see commonly owned U.S. application Ser. Nos. 07/785,624 and 07/785,623 and U.S. Pat. No. 5,180,669, issued Jan. 19, 1993, incorporated herein by reference). Furthermore, use of an amylase in the presence of oxidants, such as in bleach or peracid containing detergents, may result in partial or complete inactivation of the amylase. Therefore, the preset invention focuses on altering the oxidative sensitivity of amylases. The mutant enzymes of the present invention may also have an altered pH profile and/or altered thermal stability which may be due to the enhanced oxidative stability of the enzyme at low or high pH's.

Alpha-amylase as used herein includes naturally occurring amylases as well as recombinant amylases. Preferred amylases in the present invention are alpha-amylases derived from B. licheniformis or B. stearothermophilus, including the A4 form of alpha-amylase derived from B. licheniformis as described herein, as well as fungal alpha-amylases such as those derived from Aspergillus (i.e., A. oryzae and A. niger).

Recombinant alpha-amylases refers to an alpha-amylase in which the DNA sequence encoding the naturally occurring alpha-amylase is modified to produce a mutant DNA sequence which encodes the substitution, insertion or deletion of one or more amino acids in the alpha-amylase sequence. Suitable modification methods are disclosed herein, and also in commonly owned U.S. Pat. Nos. 4,760,025 and 5,185,258, the disclosure of which are incorporated herein by reference.

Homologies have been found between almost all endo-amylases sequenced to date, ranging from plants, mammals, and bacteria (Nakajima, R. T. et al. (1986) Appl. Microbiol. Biotechnol. 23:355–360; Rogers, J. C. (1985) Biochem. Biophys. Res. Commun. 128:470–476). There are four areas of particularly high homology in certain Bacillus amylases, as shown in FIG. 3, wherein the underlined sections designate the areas of high homology. Further, sequence alignments have been used to map the relationship between Bacillus endo-amylases (Feng, D. F. and Doolittle, R. F. (1987) J. Molec. Evol. 35:351–360). The relative sequence homology between B. stearothermophilus and B. licheniformis amylase is about 66%, as determined by Holm, L. et al. (1990) Protein engineering (3) pp. 181–191. The sequence homology between B. licheniformis and B. amyloliquefaciens amylases is about 81%, as per Holm, L. et al., supra. While sequence homology is important, it is generally recognized that structural homology is also important in comparing amylases or other enzymes. For example, structural homology between fungal amylases and bacterial (Bacillus) amylase have been suggested and, therefore, fungal amylases are encompassed within the present invention.

An alpha-amylase mutant has an amino acid sequence which is derived from the amino acid sequence of a precursor alpha-amylase. The precursor alpha-amylases include naturally occurring alpha-amylases and recombinant alpha-amylases (as defined). The amino acid sequence of the alpha-amylase mutant is derived from the precursor alpha-amylase amino acid sequence by the substitution, deletion or insertion of one or more amino acids of the precursor amino acid sequence. Such modification is of the precursor DNA sequence which encodes the amino acid sequence of the precursor alpha-amylase rather than manipulation of the precursor alpha-amylase enzyme per se. Suitable methods for such manipulation of the precursor DNA sequence include methods disclosed herein and in commonly owned U.S. Pat. Nos. 4,760,025 and 5,185,258.

Specific residues corresponding to positions M197, M15 and W138 of Bacillus licheniformis alpha-amylase are identified herein for substitution or deletion, as are all methionine, histidine, tryptophan, cysteine and tyrosine positions. The amino acid position number (i.e., +197) refers to the number assigned to the mature Bacillus lichenifonnis alpha-amylase sequence presented in FIG. 2. The invention, however, is not limited to the mutation of this particular mature alpha-amylase (*B. licheniformis*) but extends to precursor alpha-amylases containing amino acid residues at positions which are equivalent to the particular identified due in *B. licheniformis* alpha-amylase. A residue (amino acid) of a precursor alpha-amylase is equivalent to a residue of *B. licheniformis* alpha-amylase if it is either homologous (i.e., corresponding in position in either primary or tertiary structure) or analogous to a specific residue or portion of that residue in *B. licheniformis* alpha-amylase (i.e., having the same or similar functional capacity to combine, react, or interact chemically or structurally).

In order to establish homology to primary structure, the amino acid sequence of a precursor alpha-amylase is directly compared to the *B. licheniformis* alpha-amylase primary sequence and particularly to a set of residues known to be invariant to all alpha-amylases for which sequence is known, as seen in FIG. 3. It is possible also to determine equivalent residues by tertiary structure: crystal structures have been reported for porcine pancreatic alpha-amylase (Buisson, G. et al. (1987) EMBO J.6:3909–3916); Taka-amylase A from *Aspergillus oryzae* (Matsuura, Y. et al. (1984) J. Biochem. (Tokyo) 95:697–702); and an acid alpha-amylase from *A. niger* (Boel, E. et al. (1990) Biochemistry 29:6244–6249), with the former two structures being similar. There are no published structures for Bacillus alpha-amylases, although there are predicted to be common super-secondary structures between glucanases (MacGregor, E. A. & Svensson, B. (1989) Biochem. J. 259:145–152) and a structure for the *B. stearothermophilus* enzyme has been modeled on that of Taka-amylase A (Holm, L. et al. (1990) Protein Engineering 3:181–191). The four highly conserved regions shown in FIG. 3 contain many residues thought to be part of the active-site (Matsuura, Y. et al. (1984) J. Biochem. (Tokyo) 95:697–702; Buisson, G. et al. (1987) EMBO J. 6:3909–3916; Vihinen, M. et al. (1990) J. Biochem. 107:267–272) including, in the *licheniformis* numbering, His105; Arg229; Asp231; His235; Glu261 and Asp328.

Expression vector as used herein refers to a DNA construction containing a DNA sequence which is operably linked to a suitable control sequence capable of effecting the expression of said DNA in a suitable host. Such control sequences may include a promoter to effect transcription, an optional operator sequence to control such transcription, a sequence encoding suitable mRNA ribosome-binding sites, and sequences which control termination of transcription and translation. A preferred promoter is the *B. subtilis* aprE promoter. The vector may be a plasmid, a phage particle, or simply a potential genomic insert. Once transformed into a suitable host, the vector may replicate and function independently of the host genome, or may, in some instances, integrate into the genome itself. In the present specification, plasmid and vector are sometimes used interchangeably as the plasmid is the most commonly used form of vector at present. However, the invention is intended to include such other forms of expression vectors which serve equivalent functions and which are, or become, known in the art.

Host strains (or cells) useful in the present invention generally are procaryotic or eucaryotic hosts and include any transformable microorganism in which the expression of alpha-amylase can be achieved. Specifically, host strains of the same species or genus from which the alpha-amylase is derived are suitable, such as a Bacillus strain. Preferably an alpha-amylase negative Bacillus strain (genes deleted) and/or an alpha-amylase and protease deleted Bacillus strain such as *Bacillus subtilis* strain BG2473 (ΔamyE, Δapr, Δnpr) is used. Host cells are transformed or transfected with vectors constructed using recombinant DNA techniques. Such transformed host cells are capable of either replicating vectors encoding the alpha-amylase and its variants (mutants) or expressing the desired alpha-amylase.

Preferably the mutants the present invention are secreted into the culture medium during fermentation. Any suitable signal sequence, such as the aprE signal peptide, can be used to achieve secretion.

Many of the alpha-amylase mutants of the present invention are useful in formulating various detergent compositions, particularly certain dish care cleaning compositions, especially those cleaning compositions containing known oxidants. Alpha-amylase mutants of the invention can be formulated into known powdered, liquid or gel detergents having pH between 6.5 to 12.0. Suitable granular composition may be made as described in commonly owned U.S. patent application Ser. Nos. 07/429,881, 07/533,721 and 071957,973, all of which are incorporated herein by reference. These detergent cleaning compositions can also contain other enzymes, such as known proteases, lipases, celluloses, endoglycosidases or other amylases, as well as builders, stabilizers or other excipients known to those skilled in the art. These enzymes can be present as co-granules or as blended mixes or in any other manner known to those skilled in the art. Furthermore, it is contemplated by the present invention that multiple mutants may be useful in cleaning or other applications. For example, a mutant enzyme having changes at both +15 and +197 may exhibit enhanced performance useful in a cleaning product or a multiple mutant comprising changes at +197 and +138 may have improved performance.

As described previously, alpha-amylase mutants of the present invention may also be useful in the liquefaction of starch. Starch liquefaction, particularly granular starch slurry liquefaction, is typically carried out at near neutral pH's and high temperatures. As described in commonly owned U.S. application Ser. Nos. 07/788,624 and 071785,623 and U.S. Pat. No. 5,180,669, it appears that an oxidizing agent or inactivating agent of some sort is also present in typical liquefaction processes, which may affect the enzyme activity; thus, in these related patent applications an antioxidant is added to the process to protect the enzyme.

Based on the conditions of a preferred liquefaction process, as described in commonly owned U.S. application Ser. Nos. 071788,624 and 071785,623 and U.S. Pat. No. 5,180,669, namely low pH, high temperature and potential oxidation conditions, preferred mutants of the present invention for use in liquefaction processes comprise mutants exhibiting altered pH performance profiles (i.e., low pH profile, pH <6 and preferably pH <5.5), and/or altered thermal stability (i.e., high temperature, about 900°–110° C.), and/or altered oxidative stability (i.e., enhanced oxidative stability).

Thus, an improved method for liquefying starch is taught by the present invention, the method comprising liquefying a granular starch slurry from either a wet or dry milling process at a pH from about 4 to 6 by adding an effective amount of an alpha-amylase mutant of the present invention to the starch slurry; optionally adding an effective amount of an antioxidant or other excipient to the slurry; and reacting the slurry for an appropriate time and temperature to liquefy the starch.

The following is presented by way of example and is not to be construed as a limitation to the scope of the claims. Abbreviations used herein, particularly three letter or one letter notations for amino acids are described in Dale, J. W., Molecular Genetics of Bacteria, John Wiley & Sons, (1989) Appendix B.

Experimental

EXAMPLE 1

Substitutions for the Methionine Residues in *B. licheniformis* Alpha-Amylase

The alpha-amylase gene (FIG. 1) was cloned from *B. licheniformis* NCIB8061 obtained from the National Collection of Industrial Bacteria, Aberdeen, Scotland (Gray, G. et al. (1986) J. Bacteriology 166:635–643). The 1.72kb PstI-SstI fragment, encoding the last three residues of the signal sequence; the entire mature protein and the terminator region was subcloned into M13MP18. A synthetic terminator was added between the BclI and SstI sites using a synthetic oligonucleotide cassette of the form:

| BclI | | SstI | |
|---|---|---|---|
| 5' | GATCAAAACATAAAAAACCGGCCTTGGCCCCGCCGGTTTTTTATTATTTTTGAGCT | 3' | Seq ID No 1 |
| 3' | TTTTGTATTTTTTGGCCGGAACCGGGGCGGCCAAAAAATAATAAAAAC | 5' | | designed to contain the B. amyloliquefaciens subtilisin transcriptional terminator (Wells et al. (1983) Nucleic Acid Research 11:7911–7925).

Site-directed mutagenesis by oligonucleotides used essentially the protocol of Zoller, M. et al. (1983) Meth. Enzymol. 100:468–500: briefly, 5'-phosphorylated oligonucleotide primers were used to introduce the desired mutations on the M13 single-stranded DNA template using the oligonucleotides listed in Table I to substitute for each of the seven methionines found in B. licheniformis alpha-amylase. Each mutagenic oligonucleotide also introduced a restriction endonuclease site to use as a screen for the linked mutation.

TABLE 1

Mutagenic Oligonucleotides for the Substitution of the Methionine Residues in B. licheniformis Alpha-Amylase M8A     Seq ID No 2
5'-T GGG ACG CTG GCG <u>CAG TAC TTT</u> GAA TGG AT-3'
              ScaI+

M15L     Seq ID No 3
5'-TG ATG CAG <u>TAC TTT</u> GAA TGG <u>TAC CTG</u> CCC AAT GA-3'
          ScaI+             KpnI+

M197L     Seq ID No 4
5'-GAT TAT TTG TTG TAT GCC <u>GAT ATC</u>GAC TAT GAC CAT-3'
                       EcoRV+

M256A     Seq ID No 5
5'-CG GGG AAG GAG <u>GCC TTT</u> ACG GTA GCT-3'
             StuI+

M304L     Seq ID No 6
5'-GC GGC TAT GAC <u>TTA AGG</u> AAA TTG C-3'
            AflII+

M366A     Seq ID No 7
5'-C TAC GGG <u>GAT GCA</u> TAC GGG ACG A-3'
         NsiI+

M366Y     Seq ID No 8
5'-C TAC GGG GAT TAC TAC GGG <u>ACC AAG GGA</u> GAC TCC C-3'
                     StyI+

M438A     Seq ID No 9
5'-CC GGT GGG <u>GCC AAG CGG GCC</u> TAT GTT GGC CGG CAA A-3'
            SfiI+

Bold letter indicate base changes introduced by oligonucleotide.

Codon changes indicated in teh form M8A, where methionine (M) at position + 8 has been changed to alanine (A).

Underlining indicates restriction endonuclease site introduced by oligonucleotide The heteroduplex was used to transfect E. coli mutL cells (Kramer et al. (1984) Cell 38:879) and, after plaque-purification, clones were analyzed by restriction analysis of the RF1's. Positives were confirmed by dideoxy sequencing (Sanger et al. (1977) Proc. Natl. Acad. Sci. U.S.A. 74:5463–5467) and the PstI-SstI fragments for each subcloned into an E. coli vector, plasmid pA4BL.

Plasmid pA4BL

Following the methods described in U.S. application Ser. No. 860,468 (Power et al.), which is incorporated herein by reference, a silent PstI site was introduced at codon +1 (the first amino-acid following the signal cleavage site) of the aprE gene from pS168-1 (Stahl, M. L. and Ferrari, E. (1984) J. Bacter. 158:411–418). The sprE promoter and signal peptide region was then cloned out of a pJH101 plasmid (Ferrari, F. A. et al. (1983) J. Bacter. 154:1513–1515) as a HindIII-PstI fragment and subcloned into the pUC18-derived plasmid JM102 (Ferrari, E. and Hoch, J. A. (1989) Bacillus, ed. C. R. Harwood, Plenum Pub., pp. 57–72). Addition of the PstI-SstI fragment from B. licheniformis alpha-amylase gave pA4BL (FIG. 5) having the resulting aprE signal peptide-amylase junction as shown in FIG. 6.

Transformation Into B. subtilis pA4BL is a plasmid able to replicate in E. coli and integrate into the B. subtilis chromosome. Plasmids containing different variants were transformed into B. subtilis (Anagnostopoulos, C. and Spizizen, J. (1961) J. Bacter. 81:741–746) and integrated into the chromosome at the aprE locus by a Campbell-type mechanism (Young, M. (1984) J. Gen. Microbiol. 130:1613–1621). The Bacillus subtilis strain BG2473 was a derivative of 1168 which had been deleted for amylase (ΔamyE) and two proteases (Δapr, Δnpr) (Stahl, M. L. and Ferrari, E., J. Bacter. 158:411–418 and U.S. Pat. Ser. No. 5,264,366, incorporated herein by reference). After transformation the sacU32(Hy) (Henner, D. J. et al. (1988) J. Bacter. 170:296–300) mutation was introduced by PBS-1 mediated transduction (Hoch, J. A. (1983) 154:1513–1515).

N-terminal analysis of the amylase expressed from pA4BL in B. subtilis showed it to be processed having four extra alanines at the N-terminus of the secreted amylase protein ("A4 form"). These extra residues had no significant, deleterious effect on the activity or thermal stability of the A4 form and in some applications may enhance performance. In subsequent experiments the correctly processed forms of the licheniformis amylase and the variant M197T were made from a very similar construction (see FIG. 6). Specifically, the 5' end of the A4 construction was subcloned on an EcoRI-SstII fragment, from pA4BL (FIG. 5) into M13BM20 (Boehringer Mannheim) in order to obtain a coding-strand template for the mutagenic oligonucleotide below:

5'-CAT CAG CGT CCC ATT AAG ATT TGC AGC CTG CGC AGA CAT GTT GCT-3'  Seq ID No 10

This primer eliminated the codons for the extra four N-terminal alanines, correct forms being screened for by the absence of the PstI site. Subcloning the EcoRI-SstII fragment back into the pA4BL vector (FIG. 5) gave plasmid pBLapr. The M197T substitution could then be moved, on a SstII-SstI fragment, out of pA4BL (M197T) into the complementary pBLapr vector to give plasmid pBLapr (M197T). N-terminal analysis of the amylase expressed from pBLapr in *B. subtilis* showed it to be processed with the same N-terminus found in *B. licheniformis* alpha-amylase.

EXAMPLE 2

Oxidative Sensitivity of Methionine Variants

*B. licheniformis* alpha-amylase, such as Spezyme® AA20 (commercially available from Genencor International, Inc.), is inactivated rapidly in the presence of hydrogen peroxide (FIG. 7). Various methionine variants were expressed in shake-flask cultures of *B. subtilis* and the crude supernatants purified by ammonium sulphate cuts. The amylase was precipitated from a 20% saturated ammonium sulphate supernatant by raising the ammonium sulphate to 70% saturated, and then resuspended. The variants were then exposed to 0.88M hydrogen peroxide at pH 5.0, at 25° C. Variants at six of the methionine positions in *B. licheniformis* alpha-amylase were still subject to oxidation by peroxide while the substitution at position +197 (M197L) showed resistance to peroxide oxidation. (See FIG. 7.) However, subsequent analysis described in further detail below showed that while a variant may be susceptible to oxidation at pH 5.0, 250° C., it may exhibit altered/enhanced properties under different conditions (i.e., liquefaction).

EXAMPLE 3

Construction of All Possible Variants at Position 197

All of the M197 variants (M197X) were produced in the A4 form by cassette mutagenesis, as outlined in FIG. 8:

1) Site directed mutagenesis (via primer extension in M13) was used to make M197A using the mutagenic oligonucleotide below:

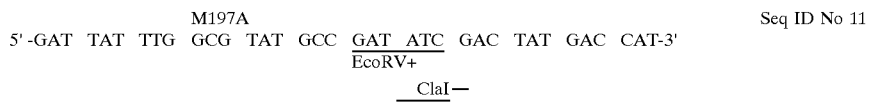

Seq ID No 11 which also inserted an EcoRV site (codons 200–201) to replace the ClaI site (codons 201-202).

2) Then primer LAAM12 (Table II) was used to introduce another silent restriction site (BstBI) over codons 186–188.

3) The resultant M197A (BstBI+, EcoRV+) variant was then subcloned (PstI-SstI fragment) into plasmid pA4BL and the resultant plasmid digested with BstBI and EcoRV and the large vector-containing fragment isolated by electroelution from agarose gel.

4) Synthetic primers LAAM14–30 (Table II) were each annealed with the largely complementary common primer LAAM13 (Table II). The resulting cassettes encoded for all the remaining naturally occurring amino acids at position +197 and were ligated, individually, into the vector fragment prepared above.

TABLE II

Synthetic Oligonucleotides Used for Cassette Mutagenesis to Produce M197X Variants

| LAAM12 | GG GAA GTT TCG AAT GAA AAC G | | Seq ID No 12 |
|---|---|---|---|
| LAAM13 | X197bs | | Seq ID No 13 |
| | (EcoRV) | GTC GGC ATA TG CAT ATA ATC ATA GTT GCC GTT TTC ATT (BstBI) | |
| LAAM14 | I197 | | Seq ID No 14 |
| | (BstBI) | CG AAT GAA AAC GGC AAC TAT GAT TAT TTG ATC TAT GCC GAC (RcoRV-) | |
| LAAM15 | F197 | | Seq ID No 15 |
| | (BstBI) | CG AAT GAA AAC GGC AAC TAT GAT TAT TTG TTC TAT GCC GAC (RcoRV-) | |
| LAAM16 | V197 | | Seq ID No 16 |
| | (BstBI) | CG AAT GAA AAC GGC AAC TAT GAT TAT TTG GTT TAT GCC GAC (RcoRV-) | |
| LAAM17 | S197 | | Seq ID No 17 |
| | (BstBI) | CG AAT GAA AAC GGC AAC TAT GAT TAT TTG AGC TAT GCC GAC (RcoRV-) | |
| LAAM18 | P197 | | Seq ID No 18 |
| | (BstBI) | CG AAT GAA AAC GGC AAC TAT GAT TAT TTG CCT TAT GCC GAC (RcoRV-) | |
| LAAM19 | T197 | | Seq ID No 19 |
| | (BstBI) | CG AAT GAA AAC GGC AAC TAT GAT TAT TTG ACA TAT GCC GAC (RcoRV-) | |
| LAAM20 | Y197 | | Seq ID No 20 |
| | (BstBI) | CG AAT GAA AAC GGC AAC TAT GAT TAT TTG TAC TAT GCC GAC (RcoRV-) | |
| LAAM21 | H197 | | Seq ID No 21 |
| | (BstBI) | CG AAT GAA AAC GGC AAC TAT GAT TAT TTG CAC TAT GCC GAC (RcoRV-) | |
| LAAM22 | G197 | | Seq ID No 22 |
| | (BstBI) | CG AAT GAA AAC GGC AAC TAT GAT TAT TTG GGC TAT GCC GAC (RcoRV-) | |
| LAAM23 | Q197 | | Seq ID No 23 |
| | (BstBI) | CG AAT GAA AAC GGC AAC TAT GAT TAT TTG CAA TAT GCC GAC (RcoRV-) | |
| LAAM24 | N197 | | Seq ID No 24 |
| | (BstBI) | CG AAT GAA AAC GGC AAC TAT GAT TAT TTG AAC TAT GCC GAC (RcoRV-) | |
| LAAM25 | K197 | | Seq ID No 25 |
| | (BstBI) | CG AAT GAA AAC GGC AAC TAT GAT TAT TTG AAA TAT GCC GAC (RcoRV-) | |
| LAAM26 | D197 | | Seq ID No 26 |
| | (BstBI) | CG AAT GAA AAC GGC AAC TAT GAT TAT TTG GAT TAT GCC GAC (RcoRV-) | |
| LAAM27 | E197 | | Seq ID No 27 |
| | (BstBI) | CG AAT GAA AAC GGC AAC TAT GAT TAT TTG GAA TAT GCC GAC (RcoRV-) | |
| LAAM28 | C197 | | Seq ID No 28 |
| | (BstBI) | CG AAT GAA AAC GGC AAC TAT GAT TAT TTG TGT TAT GCC GAC (RcoRV-) | |
| LAAM29 | W197 | | Seq ID No 29 |
| | (BstBI) | CG AAT GAA AAC GGC AAC TAT GAT TAT TTG TGG TAT GCC GAC (RcoRV-) | |
| LAAM30 | R197 | | Seq ID No 30 |
| | (BstBI) | CG AAT GAA AAC GGC AAC TAT GAT TAT TTG AGA TAT GCC GAC (RcoRV-) | |

The cassettes were designed to destroy the EcoRV site upon ligation, thus plasmids from *E. coli* transformants were screened for loss of this unique site. In addition, the common bottom strand of the cassette contained a frame-shift and encoded a NsiI site, thus transformants derived from this strand could be eliminated by screening for the presence of the unique NsiI site and would not be expected, in any case, to lead to expression of active amylase.

Positives by restriction analysis were confirmed by sequencing and transformed in *B. subtilis* for expression in shake-flask cultures (FIG. 9). The specific activity of certain of the M197X mutants was then determined using a soluble substrate assay. The data generated using the following assay methods are presented below in Table III.

Soluble Substrate Assay: A rate assay was developed based on an end-point assay kit supplied by Megazyme (Aust.) Pty. Ltd.: Each vial of substrate (p-nitrophenyl maltoheptaoside, BPNPG7) was dissolved in 10ml of sterile water, followed by a 1 to 4 dilution in assay buffer (50mM maleate buffer, pH 6.7, 5mM calcium chloride, 0.002% Tween20). Assays were performed by adding 10 $\mu$l of amylase to 790 $\mu$l of the substrate in a cuvette at 25° C. Rates of hydrolysis were measured as the rate of change of absorbance at 410nm, after a delay of 75 seconds. The assay was linear up to rates of 0.4 absorption units/min.

The amylase protein concentration was measured using the standard Bio-Rad assay (Bio-Rad Laboratories) based on the method of Bradford, M. (1976) Anal. Biochem. 72:248) using bovine serum albumin standards.

Starch Hydrolysis Assay The standard method for assaying the alpha-amylase activity of Spezyme® AA20 was used. This method is described in detail in Example 1 of U.S. Ser. No. 071785,624, incorporated herein by reference. Native starch forms a blue color with iodine but fails to do so when it is hydrolyzed into shorter dextrin molecules. The substrate is soluble lintner starch 5gm/liter in phosphate buffer, pH 6.2 (42.5gm/liter potassium dihydrogen phosphate, 3.16gm/liter sodium hydroxide). The sample is added in 25mM calcium chloride and activity is measured as the time taken to give a negative iodine test upon incubation at 30° C. Activity is recorded in liquefons per gram or ml (LU) calculated according to the formula:

$$LU/\text{ml or } LU/g = \frac{570}{V \times t} \times D.$$

TABLE III

| | SPECIFIC ACTIVITY (as % of AA20 value) on: | |
|---|---|---|
| ALPHA-AMYLASE | Soluble Substrate | Starch |
| Spezyme ® AA20 | 100 | 100 |
| A4 form | 105 | 115 |
| M15L (A4 form) | 93 | 94 |
| M15L | 85 | 103 |
| M197T (A4 form) | 75 | 83 |
| M197T | 62 | 81 |
| M197A (A4 form) | 88 | 89 |

TABLE III-continued

| ALPHA-AMYLASE | SPECIFIC ACTIVITY (as % of AA20 value) on: | |
|---|---|---|
| | Soluble Substrate | Starch |
| M197C | 85 | 85 |
| M197L (A4 form) | 51 | 17 |

EXAMPLE 4

Characterization of Variant M15L

Variant M15L made as per the prior examples did not show increased amylase activity (Table III) and was still inactivated by hydrogen peroxide (FIG. 7). It did, however, show significantly increased performance in jet-liquefaction of starch especially at low pH as shown in Table IV below.

Starch liquefaction was typically performed using a Hydroheater M 103-M steam jet equipped with a 2.5 liter delay coil behind the mixing chamber and a terminal back pressure valve. Starch was fed to the jet by a Moyno pump and steam was supplied by a 150 psi steam line, reduced to 90–100 psi. Temperature probes were installed just after the Hydroheater jet and just before the back pressure valve.

Starch slurry was obtained from a corn wet miller and used within two days. The starch was diluted to the desired solids level with deionized water and the pH of the starch was adjusted with 2% NaOH or saturated $Na_2CO_3$. Typical liquefaction conditions were:

Starch 32%-35% solids

| Starch | 32%-35% solids |
| Calcium | 40–50 ppm (30 ppm added) |
| pH | 5.0–6.0 |
| Alpha-amylase | 12–14 LU/g starch dry basis |

Starch was introduced into the jet at about 350 ml/min. The jet temperature was held at 105° –107° C. Samples of starch were transferred from the jet cooker to a 95° C. second stage liquefaction and held for 90 minutes.

The degree of starch liquefaction was measured immediately after the second stage liquefaction by determining the dextrose equivalence (DE) of the sample and by testing for the presence of raw starch, both according to the methods described in the *Standard Analytical Methods of the Member Companies of the Corn Refiners Association. Inc.*, sixth edition. Starch, when treated generally under the conditions given above and at pH 6.0, will yield a liquefied starch with a DE of about 10 and with no raw starch. Results of starch liquefaction tests using mutants of the present invention are provided in Table IV.

TABLE IV

Performance of Variants M15L (A4 form) and M15L in Starch Liquefaction

| | pH | DE after 90 Mins. |
|---|---|---|
| Spezyme ® AA20 | 5.9 | 9.9 |
| M15L (A4 form) | 5.9 | 10.4 |
| Spezyme ® AA20 | 5.2 | 1.2 |
| M15L (A4 form) | 5.2 | 2.2 |

TABLE IV-continued

Performance of Variants M15L (A4 form) and M15L in Starch Liquefaction

| | pH | DE after 90 Mins. |
|---|---|---|
| Spezyme ® AA20 | 5.9 | 9.3* |
| M15L | 5.9 | 11.3* |
| Spezyme ® AA20 | 5.5 | 3.25** |
| M15L | 5.5 | 6.7** |
| Spezyme ® AA20 | 5.2 | 0.7** |
| M15L | 5.2 | 3.65** |

*average of three experiments
**average of two experiments

EXAMPLE 5

Construction of M15X Variants

Following generally the processes described in Example 3 above, all variants at M15 (M15X) were produced in native *B. licheniformis* by cassette mutagenesis, as outlined in FIG. 12:

1) Site directed mutagenesis (via primer extension in M13) was used to introduce unique restriction sites flanking the M15 codon to facilitate insertion of a mutagenesis cassette. Specifically, a BstB1 site at codons 11–13 and a Msc1 site at codons 18–20 were introduced using the two oligonucleotides shown below.

Seq ID No 48

M15XBstB1  5'-G ATG CAG TAT TTC GAA CTGG TAT A-3'
                                   BstB1

Seq ID No 49

M15XMsc1  5'-TG CCC AAT GAT GGC CAA CAT TGG AAG-3'
                              Msc1

2) The vector for M15X cassette mutagenesis was then constructed by subcloning the Sfi1-Sstll fragment from the mutagenized amylase (BstB1+, Msc1+) into plasmid pBLapr. The resulting plasmid was then digested with BstB1 and Msc1 and the large vector fragment isolated by electroelution from a polyacrylamide gel.

3) Mutagenesis cassettes were created as with the M197X variants. Synthetic oligomers, each encoding a substitution at codon 15, were annealed to a common bottom primer. Upon proper ligation of the cassette to the vector, the Msc1 is destroyed allowing for screening of positive transformants by loss of this site. The bottom primer contains an unique SnaB1 site allowing for the transformants derived from the bottom strand to be eliminated by screening for the SnaB1 site. This primer also contains a frameshift which would also eliminate amylase expression for the mutants derived from the common bottom strand.

The synthetic cassettes are listed in Table V and the general cassette mutagenesis strategy is illustrated in FIG. 12.

TABLE V

Synthetic Oligonucleotides Used for Cassette Mutagenesis to Produce M15X Variants

| | |
|---|---|
| M15A (BstB1) C GAA TGG TAT <u>GCT</u> CCC AAT GAC GG (Msc1) | Seq ID No 50 |
| M15R (BstB1) C GAA TGG TAT <u>CGC</u> CCC AAT GAC GG (Msc1) | Seq ID No 51 |
| M15N (BstB1) C GAA TGG TAT <u>AAT</u> CCC AAT GAC GG (Msc1) | Seq ID No 52 |
| M15D (BstB1) C GAA TGG TAT <u>GAT</u> CCC AAT GAC GG (Msc1) | Seq ID No 53 |
| M15H (BstB1) C GAA TGG TAT <u>CAC</u> CCC AAT GAC GG (Msc1) | Seq ID No 54 |
| M15K (BstB1) C GAA TGG TAT <u>AAA</u> CCC AAT GAC GG (Msc1) | Seq ID No 55 |
| M15P (BstB1) C GAA TGG TAT <u>CCG</u> CCC AAT GAC GG (Msc1) | Seq ID No 56 |
| M15S (BstB1) C GAA TGG TAT <u>TCT</u> CCC AAT GAC GG (Msc1) | Seq ID No 57 |
| M15T (BstB1) C GAA TGG TAT <u>ACT</u> CCC AAT GAC GG (Msc1) | Seq ID No 58 |
| M15V (BstB1) C GAA TGG TAT <u>GTT</u> CCC AAT GAC GG (Msc1) | Seq ID No 59 |
| M15C (BstB1) C GAA TGG TAT <u>TGT</u> CCC AAT GAC GG (Msc1) | Seq ID No 60 |
| M15Q (BstB1) C GAA TGG TAT <u>CAA</u> CCC AAT GAC GG (Msc1) | Seq ID No 61 |
| M15E (BstB1) C GAA TGG TAT <u>GAA</u> CCC AAT GAC GG (Msc1) | Seq ID No 62 |
| M15G (BstB1) C GAA TGG TAT <u>GGT</u> CCC AAT GAC GG (Msc1) | Seq ID No 63 |
| M15I (BstB1) C GAA TGG TAT <u>ATT</u> CCC AAT GAC GG (Msc1) | Seq ID No 64 |
| M15F (BstB1) C GAA TGG TAT <u>TTT</u> CCC AAT GAC GG (Msc1) | Seq ID No 65 |
| M15W (BstB1) C GAA TGG TAT <u>TGG</u> CCC AAT GAC GG (Msc1) | Seq ID No 66 |
| M15Y (BstB1) C GAA TGG TAT <u>TAT</u> CCC AAT GAC GG (Msc1) | Seq ID No 67 |
| M15Z (Msc1) C GTC ATT GGG ACT ACG TAC CAT T (BstB1) (bottom strand) | Seq ID No 68 |

Underline indicates codon changes at amino acid position 15.
Conservative substitutions were made in some cases to prevent introduction of new restriction sites.

EXAMPLE 6

Bench Liquefaction with M15X Variants

Eleven alpha-amylase variants with substitutions for M15 made as per Example 5 were assayed for activity, as compared to Spezyme® AA20 (commercially available from Genencor International, Inc.) in liquefaction at pH 5.5 using a bench liquefaction system. The bench scale liquefaction system consisted of a stainless steel coil (0.25 inch diameter, approximately 350 ml volume) equipped with a 7 inch long static mixing element approximately 12 inches from the anterior end and a 30 psi back pressure valve at the posterior end. The coil, except for each end, was immersed in a glycerol-water bath equipped with thermostatically controlled heating elements that maintained the bath at 105°–106° C.

Starch slurry containing enzyme, maintained in suspension by stirring, was introduced into the reaction coil by a piston driven metering pump at about 70 ml/min. The starch was recovered from the end of the coil and was transferred to the secondary hold (95° C. for 90 minutes). Immediately after the secondary hold, the DE of the liquefied starch was determined, as described in Example 4. The results are shown in FIG. 16.

EXAMPLE 7

Characterization of M197X Variants

As can be seen in FIG. 9, there was a wide range of amylase activity (measured in the soluble substrate assay) expressed by the M197X (A4 form) variants. The amylases were partially purified from the supernatants by precipitation with two volumes of ethanol and resuspension. They were then screened for thermal stability (FIG. 10) by heating at 95° C. for 5 minutes in 10 mM acetate buffer pH 5.0, in the presence of 5 mM calcium chloride; the A4 wild-type retained 28% of its activity after incubation. For M197W and M197P we were unable to recover active protein from the supernatants. Upon sequencing, the M197H variant was found to contain a second mutation, N190K. M1 97L was examined in a separate experiment and was one of the lowest thermally stable variants. There appears to be a broad correlation between expression of amylase activity and thermal stability. The *licheniformis* amylase is restricted in what residues it can accommodate at position 197 in terms of retaining or enhancing thermal stability: cysteine and threonine are preferred for maximal thermal stability under these conditions whereas alanine and isoleucine are of intermediate stability. However, other substitutions at position +197 result in lowered thermal stability which may be useful for other applications. Additionally, different substitutions at +197 may have other beneficial properties, such as altered pH performance profile or altered oxidative stability. For example, the M197C variant was found to inactivate readily by air oxidation but had enhanced thermal stability. Conversely, compared to the M197L variant, both M197T and M197A retained not only high thermal stability (FIG. 10), but also high activity (Table III), while maintaining resistance to inactivation by peroxide at pH 5 to pH 10 (FIG. 7).

EXAMPLE 8

Stability and Performance in Detergent Formulation

The stability of the M197T (A4 form), M197T and M197A (A4 form) was measured in automatic dish care detergent (ADD) matrices. 2ppm Savinase™(a protease, commercially available from Novo Industries, of the type commonly used in ADD) were added to two commercially available bleach-containing ADD's: Cascad™(Procter and Gamble, Ltd.) and Sunlight™(Unilever) and the time course of inactivation of the amylase variants and Termamyl™(a thermally stable alpha-amylase available from Novo Nordisk, A/S) followed at 65° C. The concentration of ADD product used in both cases was equivalent to 'pre-soak' conditions: 14gm product per liter of water (7 grams per gallon hardness). As can be seen (FIGS. 11a and 11b), both form of the M197T variant were much more stable than Termamyl™ and M197A (A4 form), which were inactivated before the first assay could be performed. This stability benefit was seen in the presence or absence of starch as determined by the following protocol. Amylases were added to 5ml of ADD and Savinase™, prewarmed in a test tube and, after vortexing, activities were assayed as a function of time, using the soluble substrate assay. The "+starch" tube had spaghetti starch baked onto the sides (140° C., 60 mins.). The results are shown in FIGS. 11a and 11b.

EXAMPLE 9

Characterization of M15X Variants

All M15X variants were propagated in *Bacillus subtilis* and the expression level monitored as shown in FIG. 13. The amylase was isolated and partially purified by a 20–70% ammonium sulfate cut. The specific activity of these variants on the soluble substrate was determined as per Example 3 (FIG. 14). Many of the M15X amylases have specific activities greater than that of Spezyme® AA20. A benchtop heat stability assay was performed on the variants by heating the amylase at 90° C. for 5 min. in 50 mM acetate buffer pH 5 in the presence of 5 mM $CaCl_2$ (FIG. 15). Most of the variants performed as well as Spezyme® AA20 in this assay. Those variants that exhibited reasonable stability in this assay (reasonable stability defined as those that retained at least about 60% of Spezyme® AA20's heat stability) were tested for specific activity on starch and for liquefaction performance at pH 5.5. The most interesting of those mutants are shown in FIG. 16. M15D, N and T, along with L, out performed Spezyme® AA20 in liquefaction at pH 5.5 and have increased specific activities in both the soluble substrate and starch hydrolysis assays.

Generally, we have found that by substituting for the methionine at position 15, we can provide variants with increased low pH-liquefaction performance and/or increased specific activity.

EXAMPLE 10

Tryptophan Sensitivity to Oxidation

Chloramine-T (sodium N-chloro-p-toluenesulfonamide) is a selective oxidant, which oxidizes methionine to methionine sulfoxide at neutral or alkaline pH. At acidic pH, chloramine-T will modify both methionine and tryptophan (Schechter, Y., Burstein, Y. and Patchomik, A. (1975) Biochemistry 14 (20) 4497–4503). FIG. 17 shows the inactivation of *B. licheniformis* alpha-amylase with chloramine-T at pH 8.0 (AA20=0.65 mg/ml, M197A=1.7 mg/ml, M197L= 1.7 mg/ml). The data shows that by changing the methionine at position 197 to leucine or alanine, the inactivation of alpha-amylase can be prevented. Conversely, as shown in FIG. 18, at pH 4.0 inactivation of the M197A and M197L proceeds, but require more equivalents of chloramine-T (FIG. 18; AA20=0.22 mg/ml, M197A=4.3 mg/ml, M197L= 0.53 mg/ml; 200 mM NaAcetate at pH 4.0). This suggests that a tryptophan residue is also implicated in the chloramine-T mediated inactivation event. Furthermore, tryptic mapping and subsequent amino acid sequencing indicated that the tryptophan at position 138 was oxidized by chloramine-T (data not shown). To prove this, site-directed mutants were made at tryptophan 138 as provided below:

Preparation of Alpha-Amylase Double Mutants W138 and M197

Certain variants of W138 (F, Y and A) were made as double mutants, with M197T (made as per the disclosure of Example 3). The double mutants were made following the methods described in Examples 1 and 3. Generally,single negative strands of DNA were prepared from an M13MP18 clone of the 1.72kb coding sequence (Pst 1-Sst 1) of the *B. licheniformis* alph-amylase M197T mutant. Site-directed mutagenesis was done using the primers listed below, essentially by the method of Zoller, M. et al. (1983) except T4 gene 32 protein and T4 polymerase were substituted for klenow. The primers all contained unique sites, as well as the desired mutation, in order to identify those clones with the appropriate mutation.

Tryptophan 138 to Phenylalanine    Seq ID No 42
133 134 135 136 137 138 139 140 141 142 143
CAC CTA ATT AAA GCT TTC ACA CAT TTT CAT TTT
          Hind III Tryptophan 138 to Tyrosine    Seq ID No 43
133 134 135 136 137 138 139 140 141 142 143
CAC CTA ATT AAA GCT TAC ACA CAT TTT CAT TTT
          Hind III Seq ID No 44
Tryptophan 138 to Alanine- This primer also engineers unique sites upstream and downstream of the 138 position.
127 128 129 130 131 132 133 134 135 136 137 138
C CGC GTA ATT TCC GGA GAA CAC CTA ATT AAA GCC GCA
       BspE I 139 140 141 142 143 144 145 146 147
ACA CAT TTT CAT TTT CCC GGG CGC GGC AG
               Xma I Mutants were identified by restriction analysis and W138F and W138Y confirmed by DNA sequencing. The W138A sequence revealed a nucleotide deletion between the unique BspE 1 and Xma 1 sites, however, the rest of the gene sequenced correctly. The 1.37kb Sstll/Sstl fragment containing both W138X and M197T mutations was moved from M13MP18 into the expression vector pBLapr resulting in pBLapr (W138F, M197T) and pBLapr (WI38Y, M197T). The fragment containing unique BspE 1 and Xma 1 sites was cloned into pBLapr (BspE 1, Xma 1, M197T) since it is useful for cloning cassettes containing other amino acid substitutions at position 138.

Single Mutations at Amino Acid Position 138

Following the general methods described in the prior examples, certain single variants of W138 (F, Y, L, H and C) were made.

The 1.24kb Asp718-Sstl fragment containing the M197T mutation in plasmid pBLapr (W138X, M197T) of Example 7 was replaced by the wild-type fragment with methionine at 197, resulting in pBLapr (W138F), pBLapr (W138Y) and pBLapr (BspE 1, Xma 1).

The mutants W138L, W138H and W138C were made by ligating synthetic cassettes into the pBLapr (BspE 1, Xma 1) vector using the following primers:

---

Tryptophan 138 to Leucine    Seq ID No 45
CC GGA GAA CAC CTA ATT AAA GCC CTA ACA CAT TTT CAT TTT C
Tryptophan 138 to Histidine    Seq ID No 46
CC GGA GAA CAC CTA ATT AAA GCC CAC ACA CAT TTT CAT TTT C

| Tryptophan 138 to Cysteine | Seq ID No 47 |
|---|---|
| CC GGA GAA CAC CTA ATT AAA GCC TGC ACA CAT TTT CAT TTT C | |

Reaction of the double mutants M197T/W138F and M197T/W138Y with chloramine-T was compared with wild-type (AA20=0.75 mg/ml, M197T/W138F=0.64 mg/ml, M197T/W138Y =0.60 mg/ml; 50 mM NaAcetate at pH 5.0). The results shown in FIG. 19 show that mutagenesis of tryptophan 138 has caused the variant to be more resistant to chloramine-T.

---

What is claimed is:

1. DNA encoding a mutant alpha-amylase, the mutant alpha-amylase derived from Bacillus and comprising:

(a) a substitution of an amino acid selected from the group consisting of threonine, leucine, alanine, arginine, asparagine, aspartic acid, glutamic acid, glycine, isoleucine, lysine, phenylalanine, proline, serine, valine, histidine and glutamine or a deletion of a methionine residue at a position equivalent to M197 in *Bacillus licheniformis* alpha-amylase; and/or (b) a substitution of an amino acid selected from the group consisting of leucine, threonine, asparagine, aspartate, serine, valine, and isoleucine for a methionine residue at a position equivalent to M15 in *Bacillus licheniformis* alpha amylase.

2. Expression vectors encoding the DNA of claim 1.

3. Host cells transformed with the expression vector of claim 2.

4. A method of producing a mutant alpha-amylase with the host cell of claim 3 comprising the steps of:

(a) preparing a culture medium useful for the growth and cultivation of said host cell;

(b) cultivating said host cell under appropriate conditions to induce production of said alpha-amylase by said host cell; and (c) optionally separating said alpha-amylase from said host cells.

5. The DNA according to claim 1, wherein said alpha amylase further comprises a substitution at an amino acid equivalent to W138 in *Bacillus licheniformis* alpha-amylase.

6. DNA encoding an alpha amylase comprising an amino acid sequence corresponding to Seq. ID No. 37.

7. Expression vectors encoding the DNA of claim 6.

8. Host cells transformed with the expression vector of claim 7.

9. DNA encoding a mutant alpha amylase, wherein said alpha-amylase has an amino acid sequence of SEQ ID NO:37 with a deletion or substitution of amino acid residue M15, M197 and/or W138.

10. Expression vectors encoding the DNA of claim 9.

11. Host cells transformed with the expression vector of claim 10.

* * * * *